United States Patent [19]

Hess et al.

[11] 3,953,466

[45] Apr. 27, 1976

[54] 4(TETRAZOL-5-YL)-BUTYLTRIPHENYL-PHOSPHONIUM HALIDE COMPOUNDS

[75] Inventors: Hans-Jurgen E. Hess, Old Lyme; Leonard J. Czuba, New London; Thomas K. Schaaf, Old Lyme, all of Conn.

[73] Assignee: Pfizer Inc., New York, N.Y.

[22] Filed: July 25, 1974

[21] Appl. No.: 491,784

Related U.S. Application Data

[60] Division of Ser. No. 335,586, Feb. 26, 1973, Pat. No. 3,883,513, which is a continuation-in-part of Ser. No. 177,102, Sept. 1, 1971, abandoned.

[52] U.S. Cl............................................. 260/308 D
[51] Int. Cl.² ...................................... C07D 257/04
[58] Field of Search ................................ 260/308 D

[56] References Cited
UNITED STATES PATENTS
3,270,031    8/1966    Sherlock .......................... 260/308 D Primary Examiner—Frederick E. Waddell
Attorney, Agent, or Firm—Connolly and Hutz

[57] ABSTRACT

4(Tetrazol-5-yl)-butyltriphenylphosphonium compounds are disclosed which are useful for preparing tetrazoyl derivatives of naturally occurring prostaglandins.

5 Claims, No Drawings

4(TETRAZOL-5-YL)-BUTYLTRIPHENYLPHOS-PHONIUM HALIDE COMPOUNDS

CROSS-REFERENCE TO RELATED APPLICATION

This application is a division of application Ser. No. 335,586 as filed Feb. 26, 1973 now U.S. Pat. No. 3,883,513 which, in turn, is a continuation-in-part of our now abandoned application, Ser. No. 177,102, filed Sept. 1, 1971.

BACKGROUND OF THE INVENTION

This invention relates to certain novel analogs of the naturally occurring prostaglandins. In particular, it relates to novel 2-descarboxy-2-[tetrazol-5-yl]-ω-pentanorprostaglandins and various novel intermediates useful in their preparation.

The prostaglandins are C-20 unsaturated fatty acids which exhibit diverse physiological effects. For instance, the prostaglandins of the E and A series are potent vasodilators (Bergstrom, et al., Acta Physiol. Scand. 64:332–339, 1965 and Bergstrom, et al., Life Sci. 6:449–455, 1967). This relaxant effect on small blood vessels probably accounts for the fall in systemic arterial blood pressure (vasodepression) observed on intravenous injection of $PGE_1$ and $PGA_1$ (Weeks and King, Federation Proc. 23:327, 1964; Bergstrom, et al., 1965, op. cit.; Carlson, et al., Acta Med. Scand. 183:423–430, 1968; and Carlson, et al., Acta Physiol. Scand. 75:161–169, 1969). Another well known physiological action for $PGE_1$ and $PGE_2$ is as a bronchodilator (Cuthbert, Brit. Med. J. 4:723–726, 1969).

Another important physiological role for the natural prostaglandins is in connection with the reproductive cycle. $PGE_2$ is known to possess the ability to induce labor (Karim, et al., J. Obstet Gynaec. Brit. Cwlth. 77:200–210, 1970) and also to induce therapeutic abortion (Bygdemon, et al., Contraception, 4, 293 (1971) and to be useful for control of fertility (Karim, Contraception, 3, 1973 (1971). Patents have been obtained for several prostaglandins of the E and F series as inducers of labor in mammals (Belgian Pat. No. 754,158 and West German Pat. No. 2,034,641), and on $PGF_1$, $F_2$, and $F_3$ for control of the reproductive cycle (South African Pat. No. 69/6089.

Still other known physiological activities for $PGE_1$ are in the inhibition of gastric acid secretion (Shaw and Ramwell, In: Worcester Symp. on Prostaglandins, New York, Wiley, 1968, p. 55–64) and also of platelet aggregation (Emmons, et al. Brit. Med. J. 2:468–472, 1967).

It is now known that such physiological effects will be produced in vivo for only a short period, following the administration of a prostagladin. A substantial body of evidence indicates that the reason for this rapid cessation of activity is that the natural prostaglandins are quickly and efficiently metabolically deactivated by β-oxidation of the carboxylic acid side-chain and by oxidation of the 15α-hydroxyl group (Anggard, et al., Acta. Physiol. Scand., 81, 396 (1971) and references cited therein).

It was, of course, considered desirable to create analogs of the prostaglandins which would have physiological activities equivalent to the natural compounds, but in which the selectivity of action and the duration of the activity would be increased.

Summary of the Invention

The novel compounds of this invention, the 2-descarboxy-2-[tetrazol-5-yl]-ω-pentanorprostaglandins, in which the carboxylic acid moiety is replaced with the tetrazol ring, and in which the 15β-hydrogen may be replaced by a 15β-lower alkyl group if desired, uniquely satisfy the above mentioned requirements. That is, they possess activity profiles comparable to the parent prostaglandins and they exhibit a longer duration of action than the parent prostaglandins, and are more selective.

Novel compounds of this invention are 2-descarboxy-2-[tetrazol-5-yl]-ω-pentanorprostaglandins, and their $C_{15}$ epimers, and the corresponding 1- and 3-lower alkyltetrazolyl pentanorprostaglandins, and their $C_{15}$ epimers, having at the 15-position one hydrogen or alkyl substituent having from 1 to 3 carbon atoms and one alkyl substituent having from 5 to 11 carbon atoms, and the $C_9$, $C_{11}$, and $C_{15}$ esters thereof wherein said esterifying group is formyl, alkanoyl having from 2 to 5 carbon atoms, or benzoyl.

Preferred compounds of this invention are 2-descarboxy-2-[tetrazol-5-yl]-ω-pentanorprostaglandins of the A, E, or F series, and their $C_{15}$ epimers, and the corresponding 1- and 3-lower alkyltetrazoyl pentanorprostaglandins and their $C_{15}$ epimers, having at its 15-position one hydrogen or alkyl substituent having from 1 to 3 carbon atoms and one alkyl substituent having from 5 to 11 carbon atoms, and the $C_9$, $C_{11}$, and $C_{15}$ esters thereof wherein said esterifying group is formyl, alkanoyl having from 2 to 5 carbon atoms, or benzoyl.

Such preferred compounds are represented by the formula:

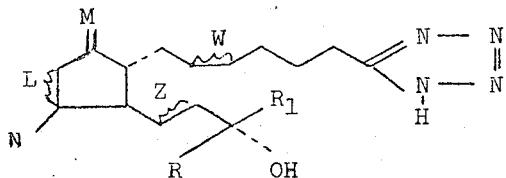

wherein R is hydrogen or alkyl having 1 to 3 carbon atoms;
$R_1$ is alkyl having from 5 to 11 carbon atoms;
W and L are each a single bond or cis double bond;
Z is single bond or trans double bond;
M is keto,

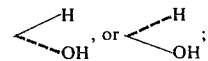

N is hydrogen or α-hydroxyl;
wherein L, M and N are so selected as to complete the structure of a prostaglandin of the A, E or F series;
and the $C_9$, $C_{11}$, and $C_{15}$ esters thereof wherein said esterifying group is formyl, alkanoyl, having from 2 to 5 carbon atoms, or benzoyl.

An especially preferred series of novel compounds are represented by the formula:

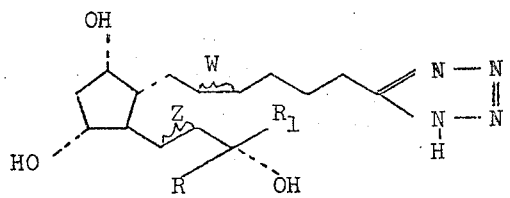

wherein R is hydrogen or alkyl having 1 to 3 carbon atoms;

R₁ is alkyl having from 5 to 11 carbon atoms;
W is a single bond or cis double bond and
Z is a single bond or trans double bond;
and the C₉, C₁₁, and C₁₅ esters thereof wherein said esterifying group is formyl, alkanoyl, having from 2 to 5 carbon atoms, or benzoyl.

Another especially preferred series of novel compounds is represented by the formula:

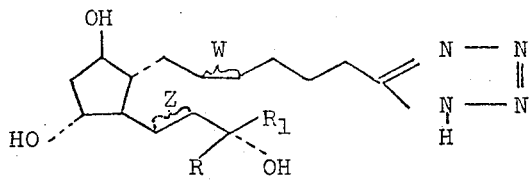

wherein R is hydrogen or alkyl having 1 to 3 carbon atoms;

R₁ is alkyl having from 5 to 11 carbon atoms;
W is a single bond or cis double bond and
Z is a single bond or trans double bond;
and the C₉, C₁₁, and C₁₅ esters thereof wherein said esterifying group is formyl, alkanoyl, having from 2 to 5 carbon atoms, or benzoyl.

Still other especially preferred novel compounds are represented by the formula:

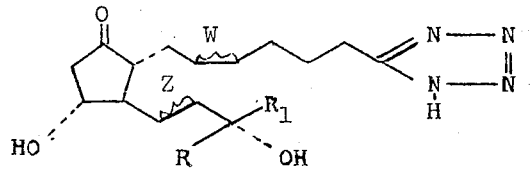

wherein R is hydrogen or alkyl having 1 to 3 carbon atoms; 1α-tetrahydropyran-

R₁ is alkyl having from 5 to 11 carbon atoms;
W is a single bond or cis double bond;
and Z is a single bond or trans double bond;
and the C₁₁, and C₁₅ esters thereof wherein said esterifying group is formyl, alkanoyl, having from 2 to 5 carbon atoms, or benzoyl.

Other especially preferred novel compounds are represented by the formula:

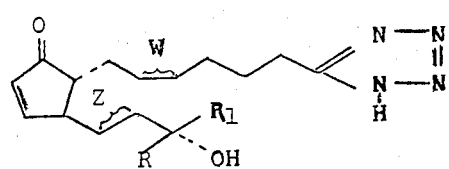

wherein R is hydrogen or alkyl having 1 to 3 carbon atoms;

R₁ is alkyl having 5 to 11 carbon atoms;
W is a single bond or cis double bond;
Z is a single bond or trans double bond;
and the C₁₅ esters thereof wherein said esterifying group is formyl, alkanoyl, having from 2 to 5 carbon atoms, or benzoyl.

The above formulas include many preferred novel prostaglandins. Among the most important of these preferred compounds are: 2-descarboxy-2-[tetrazol-5-yl]PGE₁; 2-descarboxy-2-tetrazol-5-yl]PGE₂; 2-descarboxy-2-[tetrazol-5-yl]13,14-dihydro PGE₁; 2-descarboxy-2-[tetrazol-5-yl]13,14-dihydro PGE₂; 2-descarboxy-2-[tetrazol-5-yl]PGF₁α ; 2-descarboxy-2-[tetrazol-5-yl]PGF₂α ; 2-descarboxy-2-[tetrazol-5-yl]PGF₁β ; 2-descarboxy-2-[tetrazol-5-yl]PGF₂β ; 2-descarboxy-2-[tetrazol-5-yl]PGA₁; 2-descarboxy-2-[tetrazol-5-yl]PGA₂; 15-methyl-2-descarboxy-2-[tetrazol-5-yl]PGE₂; 15-methyl-2-descarboxy-2-[tetrazol-5-yl]PGE₁; 15-methyl-2-descarboxy-2-[tetrazol-5-yl]13,14-dihydro PGE₂; 15-methyl-2-descarboxy-2-[tetrazol-5-yl]13,14-dihydro PGE₁; 15-methyl-2-descarboxy-2-[tetrazol-5-yl]PGF₂α ; 15-methyl- 2-descarboxy-2-[tetrazol-5-yl]PGF₁α ; 16,16-dimethyl-2-descarboxy-2-[tetrazol-5-yl]PGE₂; 16,16-dimethyl-2-descarboxy-2-[tetrazol-5-yl]PGE₁; 16,16-dimethyl-2-descarboxy-2-[tetrazol-5-yl]13,14-dihydro PGE₂; 16,16-dimethyl-2-descarboxy-2-[tetrazol-5-yl]13,14-dihydro PGE₁; 16,16-dimethyl-2-descarboxy-2-[tetrazol-5-yl]PGF₂α ; and 16,16-dimethyl-2-descarboxy-2-[tetrazol-5-yl]PGF₁α .

Novel reagents useful for producing the novel prostaglandins of this invention are represented by the formulae:

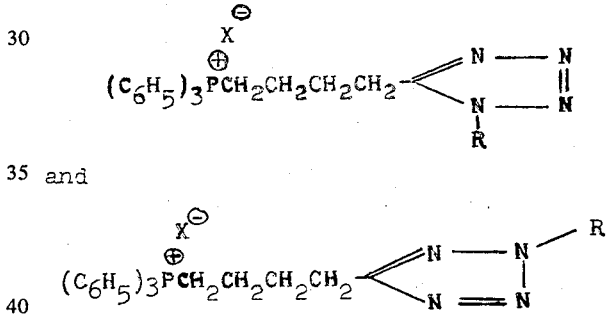

and wherein R is hydrogen or alkyl having from 1 to 3 carbon atoms; and X is chlorine, bromine, or iodine.

Especially preferred reagents include:
4-(tetrazol-5-yl)-butyltriphenylphosphonium bromide;
4-[1-N-methyl-tetrazol-5-yl]-butyltriphenylphosphonium bromide; and
4-[3-N-methyl-tetrazol-5-yl]-butyltriphenylphosphonium bromide.

Numerous novel intermediates are employed in producing the novel prostaglandins of this invention. One series of these intermediates is represented by the formula:

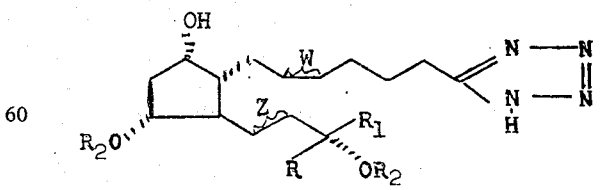

wherein R is hydrogen or alkyl having 1 to 3 carbon atoms;

R₁ is alkyl having from 5 to 11 carbon atoms;

$R_2$ is 2-tetrahydropyranyl;

W is a single bond or cis double bond;

Z is a single bond or trans double bond.

Another series of these novel intermediates is represented by the formula:

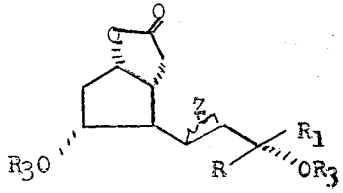

wherein R is hydrogen or alkyl having 1 to 3 carbon atoms;

$R_1$ is alkyl having from 5 to 11 carbon atoms;

Z is a single bond or a trans double bond, provided that when R is hydrogen, Z is a single bond;

$R_3$ is hydrogen or 2-tetrahydropyranyl.

Especially preferred are the cases wherein R is methyl and $R_1$ is n-amyl; R is hydrogen and $R_1$ is n-heptyl; and R is hydrogen and $R_1$ is 1,1-dimethylpent-1-yl.

Another series of novel intermediates is represented by the formula:

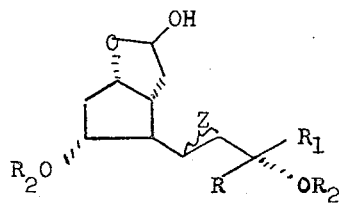

wherein R is hydrogen or alkyl having 1 to 3 carbon atoms;

$R_1$ is alkyl having from 5 to 11 carbon atoms;

$R_2$ is 2-tetrahydropyranyl; and

Z is a single bond or a trans double bond, provided that when R is hydrogen, Z is a single bond.

Especially preferred are the cases wherein R is methyl and $R_1$ is n-amyl; R is hydrogen and $R_1$ is n-heptyl; and R is hydrogen and $R_1$ is 1,1-dimethylpent-1-yl.

Another series of novel intermediates is represented by the formula:

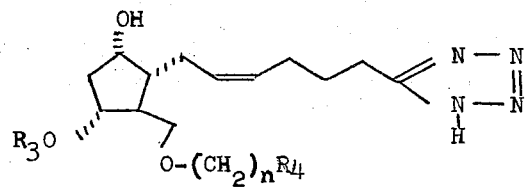

wherein $R_3$ is hydrohen or 2-tetrahydropyranyl;

$R_4$ is hydrogen, phenyl, α- or β-naphthyl, or trichloromethyl;

and n is an integer of from 1 to 3.

Another series of novel intermediates is represented by the formula:

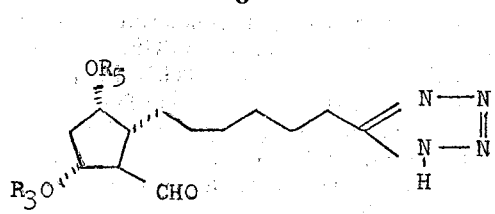

wherein $R_3$ is hydrogen or 2-tetrahydropyranyl; and $R_5$ is hydrogen, alkanoyl having from 1 to 5 carbon atoms, benzoyl, p-phenylbenzoyl, or α- or β-naphthoyl.

A final series of novel intermediates is represented by the formula:

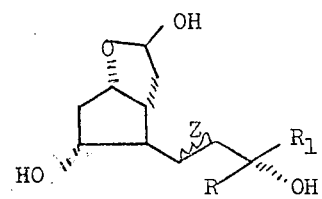

wherein R is hydrogen or alkyl having 1 to 3 carbon atoms;

$R_1$ is alkyl having from 5 to 11 carbons; and

Z is a single bond or a trans double bond, provided that when R is hydrogen, Z is a single bond.

DETAILED DESCRIPTION OF THE INVENTION

For the first step in the preparation of the above named prostaglandin analogs, the appropriate hemiacetal precursor is caused to react with the disodium salt of a novel reagent, 4-(tetrazol-5-yl)butyltriphenylphosphonium bromide, in a molar ratio of from about 1:2 to 1:5. Such precursors are as follows:

2-[5α-hydroxy-3α-(tetrahydropyran-2-yloxy)-2β-(3α-(tetrahydropyran-2-yloxy)-trans-1-octen-1-yl)cyclopent-1α-yl]-acetaldehyde, γ-hemiacetal for $PGF_{1\alpha}$, $PGF_{1\beta}$, $PGE_1$, $PGA_1$, $PGF_{2\alpha}$, $PGF_{2\beta}$, $PGE_2$, $PGA_2$, 13,14-dihydro-$PGF_{1\alpha}$, $PGF_{1\beta}$, $PGE_1$, and $PGA_1$;

2-[5α-hydroxy-3α-(tetrahydropyran-2-yloxy)-2β-(3β-lower alkyl-3α-(tetrahydropyran-2-yloxy)-trans-1-octen-1-yl)cyclopent-1α-yl]acetaldehyde, γ-hemiacetal for the 15-lower alkyl derivatives of these same prostaglandins;

2-[5α-hydroxy-3α-(tetrahydropyran-2-yloxy)-2-β-[3α-(tetrahydropyran-2-yloxy)oct-1-yl]cyclopent-1α-yl]acetaldehyde, γ-hemiacetal for 13,14-dihydro $PGF_{2\alpha}$, $PGF_{2\beta}$, $PGE_2$, and $PGA_2$;

2-[5α-hydroxy-3α-(tetrahydropyran-2-yloxy)-2β[3β-lower alkyl-3α-(tetrahydropyran-2-yloxy)-oct-1-yl]cyclopent-1α-yl]acetaldehyde, γ-hemiacetal for the 15-lower alkyl derivatives of 13,14-dihydro $PGF_{2\alpha}$, $PGF_{2\beta}$, $PGE_2$, and $PGA_2$;

2-[5α-hydroxy-3α-(tetrahydropyran-2-yloxy)-2β-(3β-(tetrahydroxypyran-2-yloxy)-trans-1-octen-1-yl)cyclopent-1α-yl]acetaldehyde, γ-hemiacetal for 15-epi-$PGF_{1\alpha}$, $PFG_{1\beta}$, $PGA_1$, $PGE_1$, $PGF_{2\alpha}$, $PGF_{2\beta}$, $PGE_2$, $PGA_2$, 13,14-dihydro-$PGF_{1\alpha}$, $PGF_{1\beta}$, $PGE_1$, and $PGA_1$;

2-[5α-hydroxy-3α-(tetrahydropyran-2-yloxy)-2β-(3α-lower alkyl-3β-(tetrahydropyran-2-yloxy)-trans-1- octen-1-yl)-cyclopent-1α-yl]acetaldehyde, γ-hemiacetal for the 15-epi-15-lower alkyl-PGF$_{1α}$, PGF$_{1β}$, PGA$_1$, PGE$_1$, PGF$_{2α}$, PGF$_{2β}$, PGE$_2$, PGA$_2$, 13,14-dihydro-PGF$_{1α}$, PMF$_{1β}$, PGE$_1$, and PGA$_1$;

2-[5α-hydroxy-3α-(tetrahydropyran-2-yloxy)-2β-(3β-(tetrahydropyran-2-yloxy)oct-1-yl)cyclopent-1α-yl]acetaldehyde, γ-hemiacetal for 15-epi-13,14-dihydro PGF$_{2α}$, PGF$_{2β}$, PGE$_2$, and PGA$_2$;

2-[5α-hydroxy-3α-(tetrahydropyran-2-yloxy-2β-(3α-lower alkyl-3β-(tetrahydropyran-2-yloxy)oct-1-yl)cyclopent-1α-yl]acetaldehyde, γ-hemiacetal for 15-epi-15-lower alkyl-13,14-dihydro PGF$_{2α}$, PGF$_{2β}$, PGE$_2$, and PGA$_2$;

and 2-[5α-hydroxy-3α-(tetrahydropyran-2-yloxy)-2β-(3α-(tetrahydropyran-2-yloxy)-cis-5-trans-1-octadien-1-yl)cyclopent-1α-yl]acetaldehyde, γ-hemiacetal for PGF$_{3α}$, PGE$_3$ and PGA$_3$.

The reaction will preferably be carried out at temperatures of about 25°-65°C. in an inert solvent such as dimethylsulfoxide and in an inert atmosphere, for a period of up to about 4 hours or until the reaction is essentially complete.

The tetrazol-containing intermediates produced in the first step, as described above, may be converted by published procedures (Corey, et al., J. Am. Chem. Soc., 93, 1490 (1971) to the tetrazoyl analogs of any of the prostaglandins listed above. These procedures are further described in detail in the appended examples and the steps entailed are summarized in the flow sheet below.

REACTION SCHEME A

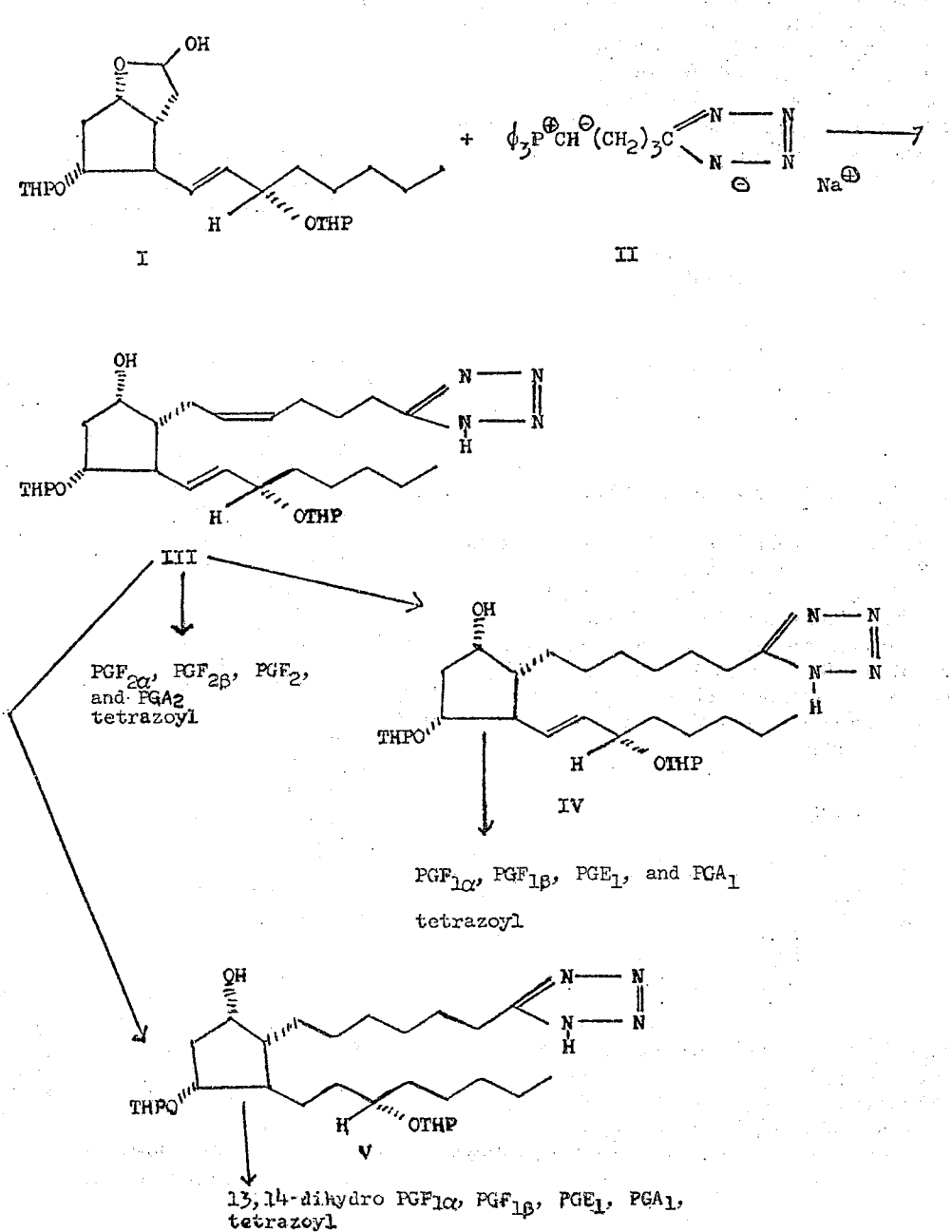

REACTION SCHEME B

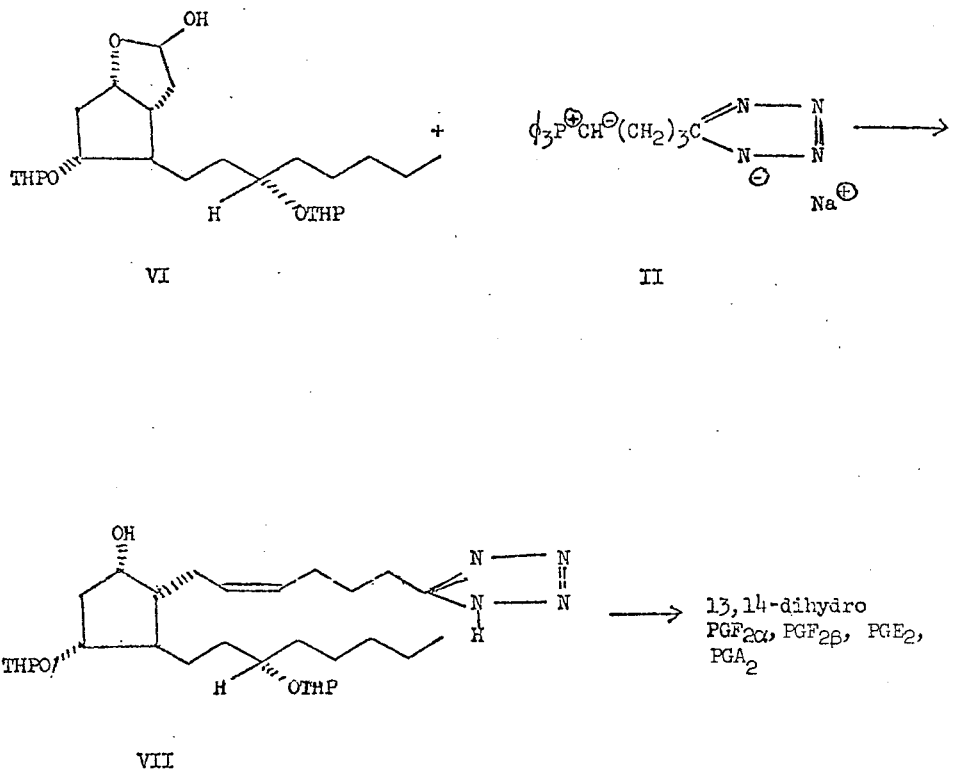

As shown in Reaction Scheme A, Hemiacetal I is caused to react with the novel reagent II to produce III, the tetrazoyl analog of the bis-THP ether of PGF$_{2\alpha}$.

III → PGF$_{2\alpha}$-tetrazoyl involves hydrolysis with aqueous acetic acid, concentration, and purification by column chromatography.

III → PGE$_2$-tetrazoyl requires treatment with Jones reagent to form a second intermediate before the acid treatment and purification as above.

PGF$_{2\beta}$-tetrazoyl is obtained by treating PGE$_2$-tetrazoyl with sodium borohydride, hydrolysis, concentration, and purification by column chromatography.

PGA$_2$-tetrazoyl is obtained by treating PGE$_2$-tetrazoyl with formic acid, concentration, and purification by column chromatography.

III → PGF$_{1\alpha}$-tetrazoyl requires a reduction with palladium on carbon and methanol to produce IV which may then be hydrolysed with aqueous acetic acid, and purified as above.

III → PGE$_1$-tetrazoyl → PGF$_{1\beta}$-tetrazoyl follows exactly the same method as outlined for the PGE$_2$ → PGF$_{2\beta}$ series above.

III → PGE$_1$-tetrazoyl → PGA$_1$-tetrazoyl follows exactly the same method as outlined for the PGE$_2$ PGA$_2$ series above.

III → 13,14-dihydro PGF$_{1\alpha}$ requires a reduction with palladium on carbon and methanol to produce V which is then hydrolysed with aqueous acetic acid, and purified as above. To produce the other 13,14-dihydro derivatives one follows the procedures outlined above.

Referring now to Reaction Scheme B, Hemiacetal VI is caused to react with the novel reagent II to produce VII, the tetrazoyl analog of the bis-THP ether of 13,14-dihydro PGF$_{2\alpha}$.

VII → 13,14-dihydro PGF$_{2\alpha}$-tetrazoyl involves hydrolysis with aqueous acetic acid, concentration, and purification by column chromatography.

VII → 13,14-dihydro PGE$_2$-tetrazoyl requires treatment with Jones reagent to form a second intermediate before acid treatment and purification as above.

To obtain 13,14-dihydro PGF$_{2\beta}$, one follows the sequence above for PGE$_{20}$ → PGF$_{2\beta}$.

13,14-dihydro PGA$_2$-tetrazoyl is obtained by treating 13,14-dihydro PGE$_2$-tetrazoyl with formic acid, concentrating, and purifying by column chromatography.

To produce the 15-epimeric, 15-lower alkyl derivatives, or 15-epimeric-15-lower alkyl derivatives of all of the above mentioned prostaglandin tetrazoyls, one merely employs hemiacetal VIII – XIII, and proceeds as above to produce the desired compound.

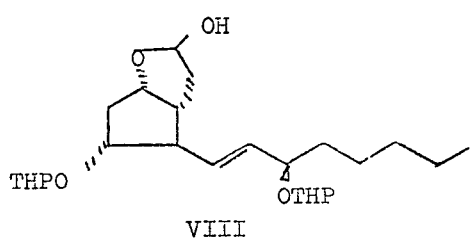
VIII

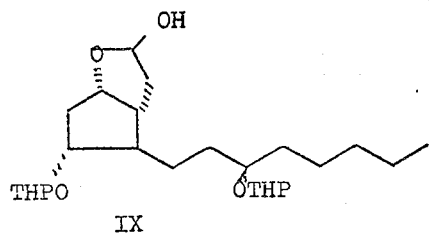
IX

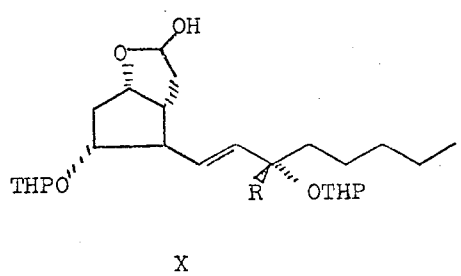
X

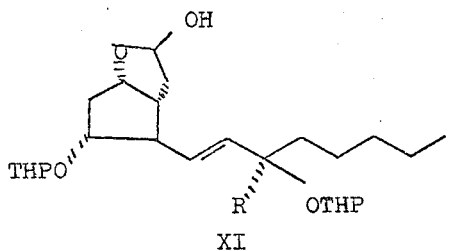
XI

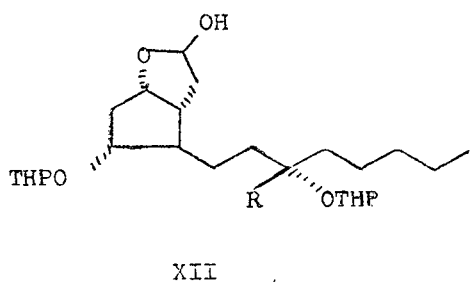
XII

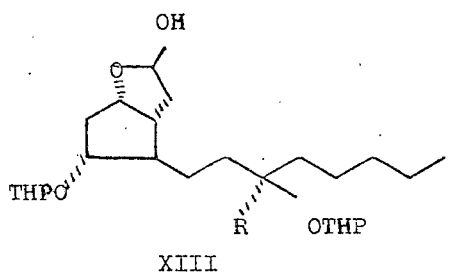
XIII

To produce PGF$_{3\alpha}$, PGE$_3$, and PGA$_3$ tetrazoyl, hemiacetal XIV is employed as the starting material and all of the other reaction steps are identical to those given above.

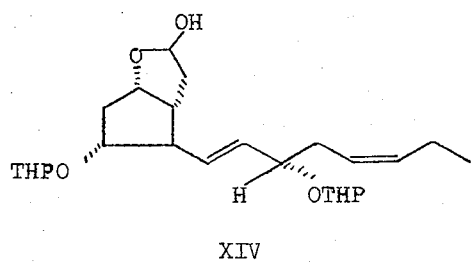
XIV

Other intermediates may be employed in alternate preparations of the above named prostaglandin analogs. The PGF-tetrazoyls may be prepared directly by causing the appropriate hemiacetal precursor to react with the disodium salt of a novel reagent, 4-(tetrazol-5-yl)butyltriphenylphosphonium bromide, in a molar ratio of from about 1:4 to 1:7. Such precursors are as follows:

2-[3α,5α-dihydroxy-2β-(3α-hydroxy-trans-1-octen-1-yl)-cyclopent-1α-yl]acetaldehyde, γ-hemiacetal for PGF$_{2\alpha}$, PGF$_{1\alpha}$, and 13,14-dihydro PGF$_{1\alpha}$;

2-[3α,5α-dihydroxy-2β-(3β-hydroxy-trans-1-octen-1-yl)1cyclopent-1α-yl]acetaldehyde, γ-hemiacetal for 15-epi-PMF2$_\alpha$, PGF$_{1\alpha}$, and 13,14-dihydro PGF$_{1\alpha}$;

2-[3α,5α-dihydroxy-2β-(3β-lower alkyl-3α-hydroxy-trans-1-octen-1-yl)cyclopent-1α-yl]acetaldehyde, γ-hemiacetal for 15-lower alkyl-PGF$_{2\alpha}$, PGF$_{1\alpha}$, and 13,14-dihydro PGF$_{1\alpha}$;

2-]3α,5α-dihydroxy-2β-(3α-lower alkyl-3β-hydroxy-trans-1-octen-1-yl)cyclopent-1α-yl]acetaldehyde, γ-hemiacetal for 15-epi-15-lower alkyl-PGF$_{2\alpha}$, PGF$_{1\alpha}$, and 13,14-dihydro PGF$_{1\alpha}$;

2-[3α,5α-dihydroxy-2β-(3α-hydroxyoct-1-yl)cyclopent-1-yl]acetaldehyde, γ-hemiacetal for 13,14-dihydro PGF$_{2\alpha}$;

2-[3α,5α-dihydroxy-2β-(3β-hydroxyoct-1-yl)cyclopent-1α-yl]acetaldehyde, γ-hemiacetal for 15-epi-13,14-dihydro PGF$_{2\alpha}$;

2-[3α,5α-dihydroxy-2β-(3β-lower alkyl-3α-hydroxyoct-1-yl)-cyclopent-1α-yl]acetaldehyde, γ-hemiacetal for 15-lower alkyl-13,14-dihydro PGF$_{2\alpha}$;

2-[3α,5α-dihydroxy-2β-(3α-lower alkyl-3β-hydroxyoct-1-yl)-cyclopent-1α-yl]acetaldehyde, γ-hemiacetal for 15-epi-15-lower alkyl-13,14-dihydro PGF$_{2\alpha}$.

The reaction will preferably be carried out at temperatures of about 25°–65° in a solvent such as dimethylsulfoxide, and under an inert atmosphere, for a period of up to 4 hours until the reaction is essentially complete. Dilution with water, acidification extraction, concentration, and purification by column chromatography affords the PGF tetrazoyl analogs.

The PGF$_{1\alpha}$, PGF$_{1\beta}$, PGE$_1$, and PGA$_1$ tetrazoyl analogs may be prepared by the alternate synthesis summarized in flow sheet C. For the first step in the preparation of the above named prostaglandin analogs, the hemiacetal 25α-hydroxy-3α-(tetrahydropyran-2-yloxy)-2β-benzyloxymethyl cyclopent-1α-yl]-acetaldehyde, γ-hemiacetal is caused to react with the disodium salt of a novel reagent, 4-(tetrazol-5-yl)butyltriphenylphosphonium bromide as described above. This tetrazol-containing intermediate may be converted by published procedures (Corey, Schaaf, J. Org. Chem., 37, 2921 (1972)) as described in detail in the appended examples as summarized below.

As shown in Reaction Scheme C, hemiacetal XV is caused to react with the novel reagent II to produce XVI.

XVI → XVII involves treatment with acetic anhydride and pyridine to form a second intermediate, reduction with hydrogen and palladium on carbon ion acetic acid:ethanol to form a third intermediate, and oxidation with Collins' reagent.

REACTION SCHEME C

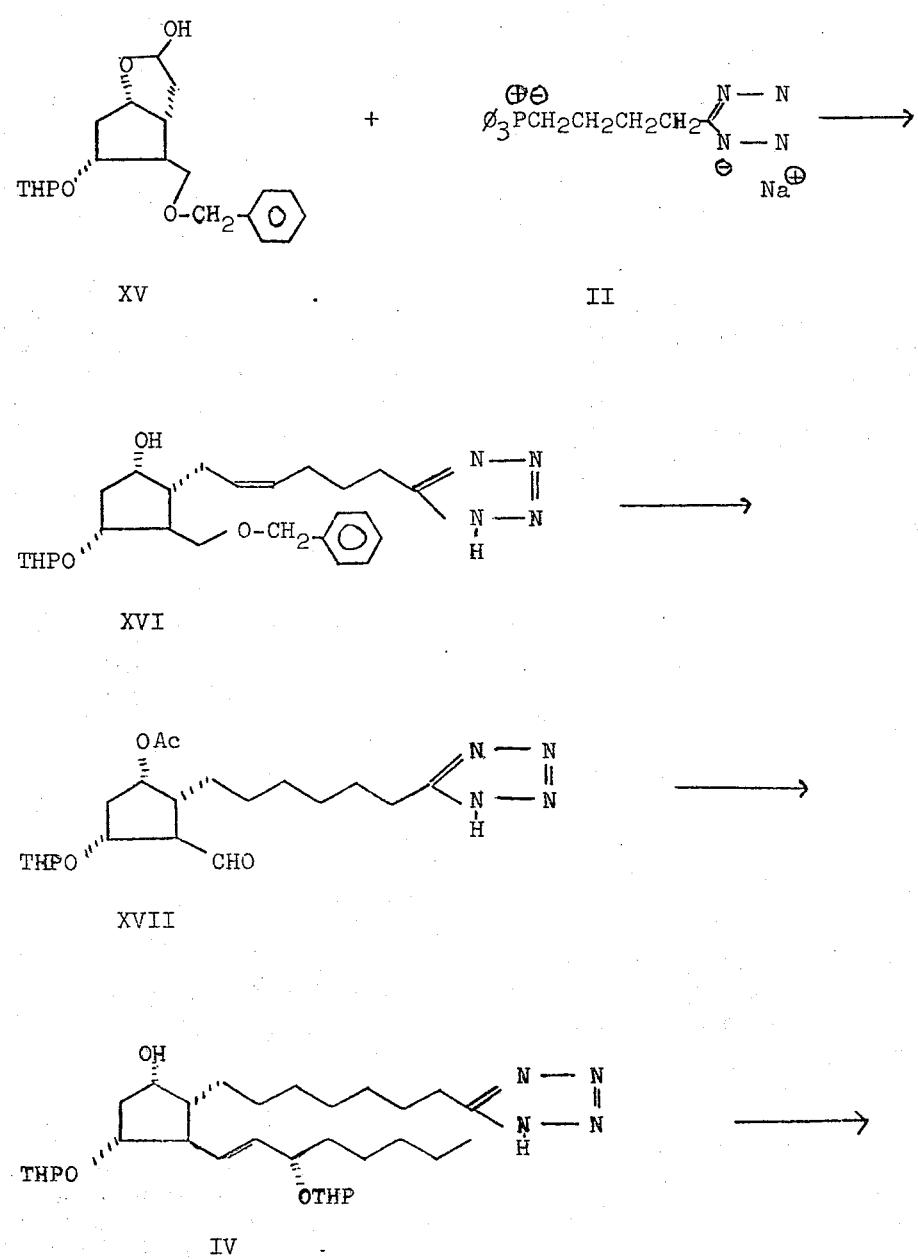

XVII → IV requires treatment with the sodium salt of dimethyl 2-oxoheptylphosphonate to form a second intermediate, reduction with lithium tris-sec-butylborohydride to form a third intermediate, treatment with dihydropyran to form a fourth intermediate, and treatment with aqueous sodium hydroxide.

IV → $PGE_1$, $PGF_{1\alpha}$, $PGF_{1\beta}$, and $PGA_1$ tetrazoyl one follows the procedure outlined above.

The tetrazoyl analogs described above may be transformed into other types of derivatives. For example, treatment of $PGE_2$-tetrazoyl with an ethereal solution of diazomethane followed by concentration and column chromatography provides both the $PGE_2$ 1-N-methyltetrazoyl and the $PGE_2$ 3-N-methyltetrazoyl. Furthermore, the 9,11,15-triesters of the PGF-tetrazoyls or the 11,15-bis esters of the PGE-tetrazoyls may be prepared by treatment of the parent compound with the appropriate acid chloride or acid anhydride in the presence of a base such as pyridine. These procedures are further described in detail in the appended examples.

Lower side-chain modified prostaglandin tetrazoyls, i.e. bis-ω-homo $PGF_{2\alpha}$ tetrazoyl or 16,16-dimethyl $PGE_2$ tetrazoyl, may be prepared starting with the appropriately substituted hemiacetal and the several procedures described above. These procedures are further elaborated in detail in the appended examples.

As the literature cited under "Background of the Invention" establishes, the natural prostaglandins are known to exhibit a spectrum of physiological activities. In numerous in vivo and in vitro tests we have demonstrated that the tetrazoyl prostaglandin analogs possess the same physiological activities as the natural prostaglandins with greater selectivity of action. These tests include, among others, a test for effect on isolated smooth muscle from rabbit aorta and guinea pig ileum, a test for inhibition of norepinephrine induced lipolysis in isolated rat fat cells, a test for effect on histamine induced bronchospasm in guinea pig, a test for effects on dog blood pressure, and a test for effects on rat blood pressure.

To examplify the greater tissue selectivity of the tetrazoyl derivatives, the threshold dose for spasmogenic effect on isolated smooth muscle from rabbit aorta, was found to be 250 ng/ml for $PGE_2$ and 500 ng/ml for $PGE_2$-tetrazoyl. In this same test using guinea pig ileum, values of 20 ng/ml and 100 ng/ml were obtained for the same two compounds.

In the test for effects on dog blood pressure, both $PGE_2$ and $PGE_2$-tetrazoyl were found to be depressors and values of 0.16 μg/kg and 0.8 μg/kg were obtained on the two compounds as the threshold dose for this effect.

In contrast, in the test for protection by 100 μg/ml of the test compound against histamine induced bronchospasm in guinea pigs, values of 65–75% were obtained for both $PGE_2$ and $PGE_2$-tetrazoyl. Thus, $PGE_2$-tetrazoyl appears to be a more tissue selective bronchodilator than $PGE_2$.

That the duration of the action of the 15β-lower alkyl tetrazoyl analogs is increased over that of the parent prostaglandin is clearly illustrated by the data in Table I below. This experiment demonstrates that a comparable drop in the blood pressure of anesthetized dogs was achieved with a comparable i.v. administered dose of the natural prostaglandin $PGE_2$ or its tetrazoyl analog. In the case of the 15-methyl $PGE_2$ tetrazoyl analog, while the size of the dose must be increased to achieve an equivalent drop in blood pressure, the length of time that this reduced pressure is maintained is increased dramatically.

TABLE I

| Dog No. | Compound Used | Dose μg/kg IV | Pre[1] | Post[2] | mm Hg | Recovery Time Min. |
|---|---|---|---|---|---|---|
| 1 | $PGE_2$ | 4 | 138 | 110 | 28 | 25 |
| | $PGE_2$-Tetrazoyl | 4 | 138 | 110 | 28 | 31 |
| | 15-Methyl-$PGE_2$-Tetrazoyl | 50 | 135 | 108 | 27 | 37 |
| 2 | $PGE_2$ | 2 | 130 | 92 | 38 | 4 |
| | $PGE_2$-Tetrazoyl | 2 | 125 | 95 | 30 | 6 |
| | 15-Methyl-$PGE_2$-Tetrazoyl | 50 | 128 | 93 | 35 | 26 |
| 3 | $PGE_2$ | 2 | 115 | 92 | 23 | 6 |
| | $PGE_2$-Tetrazoyl | 2 | 114 | 90 | 24 | 10 |
| | 15-Methyl-$PGE_2$-Tetrazoyl | 50 | 114 | 90 | 24 | 120 |
| 4 | $PGE_2$ | 2 | 130 | 100 | 30 | 6 |
| | $PGE_2$-Tetrazoyl | 2 | 132 | 110 | 22 | 6 |
| | 15-Methyl-$PGE_2$-Tetrazoyl | 50 | 136 | 103 | 33 | 30 |
| 5 | $PGE_2$ | 2 | 115 | 82 | 33 | 5 |
| | $PGE_2$-Tetrazoyl | 2 | 110 | 90 | 30 | 8 |
| | 15-Methyl-$PGE_2$-Tetrazoyl | 50 | 120 | 92 | 28 | 40 |

[1] Blood pressure before administration of drug.
[2] Blood pressure after administration of drug.

The new compounds of this invention can be used in a variety of pharmaceutical preparations and they may be administered by a variety of routes, such as intravenous, oral and topical including aerosol, intravaginal, and intranasal among others. The dosage amounts and dosage routes for the new compounds of the invention generally are equivalent to those of the corresponding natural prostaglandins for the selected utility. This is verified by the following exemplary dosage forms and amounts illustrated below for specific compounds.

The natural prostaglandins of the E and F series are well known agents for the induction of abortion, and the corresponding tetrazoyl prostaglandins share this utility. For such treatment an aqueous suspension of $PGE_2$ or $PGE_{2\alpha}$-tetrazoyl is appropriately administered at a level of from about 0.2–5.0 mg/dose for $PGE_2$-tetrazoyl or 3.0–50 mg/dose for $PGF_{2\alpha}$-tetrazoyl with from 1 to 7 oral doses per day being employed in either case.

If a intravaginal treatment for abortion induction is desired, a suitable agent is a sterile ethanolic solution of either of these two tetrazoyl prostaglandins or lactose tablets of the same two agents. In such treatments suitable doses are from 15–200 mg/dose for $PGE_2$-tetrazoyl or from 35–250 mg/dose for $PGF_{2\alpha}$-tetrazoyl with 1 or 2 doses being employed.

In cases where a midterm abortion is necessary, an effective agent is an ethanol-dextrose solution of $PGE_2$-tetrazoyl administered as an intravenous infusion. A suitable dosage is from about 5–500 $\mu$g/min administered for a period of from 1–24 hours.

If an intra-amniotic treatment for midterm abortion is necessary, an effective agent is a sterile ethanolic solution of either $PGE_2$ or $PGF_{2\alpha}$-tetrazoyl administered directly into the amniotic sac by means of a polyethylene catheter. A suitable dose is from 0.5–5.0 mg/dose for $PGE_2$-tetrazoyl or 5–50 mg/dose for $PGF_{2\alpha}$-tetrazoyl with from 1 to 5 doses administered.

Another use for the tetrazoyl prostaglandins is as an inducer of labor. For this purpose an ethanol-saline solution of $PGE_2$-tetrazoyl is employed as an intravenous infusion in the amount of from about 3–100 $\mu$g/kg/min for from 1–10 hours.

Still other applications for the E-series prostaglandin-tetrazoyls are to produce bronchodilation or to increase nasal patency. An appropriate dosage form for this use is an aqueous ethanolic solution of $PGE_2$ or $PGE_1$-tetrazoyl which for bronchodilator use is employed as an aerosol using fluorinated hydrocarbons as propellant in the amount of from about 3–500 $\mu$g/dose.

A use for A- series tetrazoyl prostaglandins is an antihypertensive agents. For such a treatment an ethanol solution of $PGA_1$ or $PGA_2$-tetrazoyl is appropriately administered as an intravenous infusion at about 1–30 $\mu$g/kg/min for a total dose of from 1–20 mg/kg/day.

The utility and dosage amounts of the 15-lower alkyl substituted tetrazoyl prostaglandins generally parallels that of the 15-desalkyl derivatives.

To prepare any of the above dosage forms or any of the numerous other forms possible, various reaction-inert diluents, excipients or carriers may be employed. Such substances include, for example, water, ethanol, gelatins, lactose, starches, magnesium stearate, talc, vegetable oils, benzyl alcohols, gums, polyalkylene glycols, petroleum jelly, cholesterol, and other known carriers fo medicaments. If desired, these pharmaceutical compositions may contain auxiliary substances such as preserving agents, wetting agents, stabilizing agents, or other therapeutic agents such as antibiotics.

It will be seen that the formulae appearing in the foregoing depict optically active compounds. It will be clear, however, that the corresponding racemates will exhibit valuable biological activity by virtue of their content of the above-mentioned biologically active optical isomer, and it is intended that such racemates also be embraced by the foregoing formulae herein and in the appended claims. The racemic mixtures are readily prepared by the same methods employed herein to synthesize to optically active species, by mere substitution of corresponding racemic precursors in place of optically active starting materials.

The following examples are merely illustrative, and in no way limit the scope of the appended claims. All temperatures are given in degree Centigrade and all percentages are by weight.

EXAMPLE I

A mixture of 5-bromovaleronitrile (16.2 g., 0.10 mole), triphenylphosphine (26.2 g., 0.10 mole) and toluene (100 ml.) was heated to reflux with stirring under nitrogen for 16 hours. The resulting thick white suspension was cooled to room temperature and filtered. The residue was washed with benzene and air dried to give 33.0 g. of a white, crystalline solid, m.p. 230°–232°, which was 4-cyanobutytriphenylphosphonium bromide.

Anal. Calc'd for $C_{23}H_{23}BrNP$: C, 65.10; H, 5.47; N, 3.30. Found: C, 65.01; H, 5.40; N, 3.19.

A mixture of the phosphonium salt above (10.0 g., 23.5 mmoles), ammonium chloride (1.60 g., 30.0 mmoles), lithium chloride (0.032 g., 0.76 mmole), sodium azide (1.91 g., 29.3 mmoles), and dimethylformamide (50 ml.) was heated to 127° (oil bath) under nitrogen with stirring for 18 hours. The resulting suspension was cooled and filtered. The residue was washed with dimethylformamide and the combined filtrate and washings were concentrated (aspirator pressure, ca. 45°). The oily residue was crystallized from water at 0° and air dried to give a white crystalline solid (8.11 g.), m.p. 100°–102°. The product was recrystallized from methanol-ether to give white prisms (7.18 g.), m.p. 197°–206°. An analytical sample was prepared by recrystallization from 2-propanol to give a white crystalline powder, m.p. 212°–213°, which was 4-(tetrazol-5-yl)butyltriphenylphosphonium bromide.

Anal. Calc'd for $C_{23}H_{24}H_4PBr$: C, 59.10; H, 5.17; N, 11.99; P, 6.63; Br, 17.09. Found: C, 59.35; H, 5.28; N, 12.31; P, 6.78; Br, 17.26.

EXAMPLE II

Sodium hydride mineral oil dispersion (56.6%, 2.12 g., 1.20 g. dry powder) was washed with three portions of pentane under dry nitrogen. The resulting gray powder was stirred with dry dimethylsulfoxide (25 ml., distilled from $CaH_2$, bp ca. 60° to 6 mm) under nitrogen at 60°–65° for 2 hours to give a cloudy, gray solution. The solution was cooled, and an aliquot was diluted with water and was titrated to a phenolphthalien end point with 0.100N hydrochloric acid to determine a molarity of 2.07. A portion of the standardized solution (5.36 ml., 11.1 mmoles) was added dropwise over a 15 min. period to a stirred solution of the final phosphonium salt of Example I (2.70 g., 5.78 mmoles) in dry dimethylsulfoxide (8 ml.) under nitrogen at room temperature. To the resulting red solution was added a solution of 2-[5α-hydroxy-3α-(tetrahydropyran-2-yloxy)-2β-(3α-tetrahydropyran-2-yloxy)-trans-1-octen-1-yl)cyclopent- 1α-yl]acetaldehyde, γ-hemiacetal [known compound, see E. J. Corey, et al., J. Am. Chem. Soc., 92, 397 (1970), 1.00 g., 2.28 mmoles] in dimethylsulfoxide (6 ml.) over a 50 min. period while stirring the mixture under nitrogen at room temperature. The mixture was stirred for an additional 2½ hours and then was poured into ice-water (100 ml.). The aqueous mixture was acidified with 1.0N hydrochloric acid (11.8 ml.) and extracted with three 50-ml. portions of ethyl acetate. The extract was washed with water (20 ml.), dried (MgSO$_4$), and concentrated (aspirator pressure, ca. 40°) to give a red oil (2.51 g.). The crude oil was chromatographed on 60–200 mesh silica gel (50 g.) using chloroform, ethyl acetate and methanol as successive eluents to separate a mixture containing mostly triphenylphosphine oxide (1.05 g.), unchanged starting material (0.18 g., 18% recovery), the expected product, 3β-[3α-(tetrahydropyran-2-yloxy)-trans-1-octe-1-yl]-2α-[6-(tetrazol-5-yl)-cis-2-hexen-1-yl]-4α-(tetrahydropyran-2-yloxy)cyclopentan-1α-ol as a thick colorless oil (0.650 g., 50.5% yield), and a mixture of expected product and unidentified products (0.459 g.). The fractions were identified by thin layer chromatography on neutral silica gel glass plates using ethyl acetate or chloroform-methanol (5:1) as developer and the chromatograms were visualized by heating with a vanillin-phosphoric acid reagent. The expected product exhibited $R_f$ values of 0.22 and 0.72, respectively, with these two developing systems. This compound is an important intermediate in the synthesis of tetrazoyl analogs of several prostaglandins, as is illustrated below.

EXAMPLE III

A mixture of the bis THP ether of Example II (333 mg., 0.614 mmoles), acetic acid (6.5 ml.) and water (3.5 ml.) was stirred under nitrogen for 4 hours a 40°–45°. The resulting clear solution was concentrated (aspirator pressure, ca. 40°) and the residue (335 mg.) was partitioned between water (20 ml.) and ethyl acetate (20 ml.). The ethyl acetate layer was separated and combined with an ethyl acetate extract (20 ml.) of the aqueous layer. The combined ethyl acetate solution were washed with brine (20 ml.), dried (Na$_2$SO$_4$) and concentrated (aspirator pressure ca. 40°) leaving a clear, faintly tan oil (223 mg.). The oil was chromatographed on acidic silica gel (10 g., Malinckrodt Silicar CC-4, 100–200 mesh) using chloroform followed by mixtures of chloroform and methanol as eluents to separate an unidentified mixture (87 mg.) and the desired product, 3β-(3α-hydroxy-trans-1-octen-1-yl)-2α-[6-(tetrazol-5-yl)-cis-2-hexen-1-yl]-cyclopentan-1α,4α-diol, as a thick colorless oil (103 mg., yield 44%). Thin layer chromatograph of product on silica gel glass plates using chloroform-methanol (5:1) as the developer and visualizing the chromatogram by heating with vanillin-phosphoric acid reagent showed a single spot at $R_f$ 0.13. This product is 2-descarboxy-2-(tetrazol-5-yl) PGF$_{2\alpha}$.

The above product may be hydrogenated as described in Example VA to provide 3β-(3α-hydroxyoct-1-yl)-2α-[6-(tetrazol-5-yl)hex-1-yl]cyclopentan-1α,4α-diol.

EXAMPLE IA

To a solution of the 4-(tetrazol-5-yl)butyltriphenylphosphonium bromide prepared in Example I (4.65 g.; 10.0 m moles) in 50 ml. of dry tetrahydrofuran is added a solution of diazomethane in ether until the reaction solution remains yellow for 5 minutes. Concentration followed by chromatographic purification affords the desired 4-(1-N-methyltetrazol-5-yl)butyltriphenylphosphonium bromide and 4-(3-N-methyltetrazol-5-yl)butyltriphenylphosphonium bromide.

These compounds may be converted by methods both known (see: E. J. Corey, et al., J. Am. Chem. Soc., 92, 397 (1970) and described herein to the 2-descarboxy-2-(1-N-methyltetrazol-5-yl) and 2-descarboxy-2-(3-N-methyltetrazol-5-yl)prostaglandins.

EXAMPLE IV

To a stirred solution of the bis THP ether of Example II (400 mg., 0.731 mmoles) in acetone (12.3 ml.) at −10° was added, dropwise over a 5 minute period, 0.29 ml. of Jones reagent previously prepared from 2.67 g. chromium trioxide and 2.3 ml. concentrated sulfuric acid diluted to 10 ml. volume with water. The resulting mixture was aged for 15 minutes at −10° and then treated with isopropyl alcohol (0.46 ml.). The mixture was stirred for an additional 5 minutes at −10° and partitioned between ethyl acetate (30 ml.) and water (30 ml.). The ethyl acetate layer was separated and combined with an ethyl acetate extract of the aqueous layer. The combined solutions were washed with three 15-ml. portions of water, dried (MgSO$_4$), and concentrated (aspirator pressure, ca. 40°–50°) leaving 358 mg. of 4α-(tetrahydropyran-2-yloxy)-3β-[3α-(tetrahydropyran-2-yloxy)-trans-1-octen-1-yl]-2α-[6-(tetrazol-5-yl)-cis-2-hexen-1-yl]cyclopentanone as a viscous oil.

EXAMPLE V

The oil produced in Example IV was stirred with acetic acid (10.7 ml.) and water (5.8 ml.) under nitrogen at 40°–45° for 3 hours. The resulting solution was concentrated (aspirator pressure, ca. 40°–50°) and the residue (275 mg.) was chromatographed on acidic silica gel (25 g., Malinckrodt Silicar CC-4, 100–200 mesh) using mixtures of chloroform and methanol as the eluent to separate an unidentified mixture (130 mg.) and the desired product, 4α-hydroxy-3β-(3α-hydroxy-trans-1-octen-1-yl)-2α-[6-(tetrazol-5-yl)-cis-2-hexen-1-yl]cyclopentanone, as a clear, thick, colorless oil (103 mg., 37%). Thin layer chromatography of the product on silica gel glass plates using methylene chloride-methanol (9:1) or benzene-tetrahydrofuran-formic acid (15:5:2) as the developers and visualizing the chromatograms by heating with vanillin-phosphoric acid reagent showed a single spot with $R_f$ values of 0.30 and 0.25 on the two systems, respectively. Their ir spectrum (CHCl$_3$) of the product exhibited a strong absorption band at 1,730 cm$^{-1}$ (C=O) and a moderately weak band at 3,610 cm$^{-1}$ (OH). The uv spectrum (95% EtOH) of the product showed only end absorption. This product is 2-descarboxy-2-(tetrazol-5-yl)PGE$_2$. Treatment of a small sample of the product with 10% aqueous sodium hydroxide and ethanol for 15 minutes at room temperature gave a single product by tlc ($R_f$ 0.38, silica gel, benzene-tetrahydrofuran-formic acid, 15:5:2). The uv spectrum (95% EtOH) of the latter product exhibited an absorption maximum at 279 mμ (19,600).

EXAMPLE VA

A heterogeneous mixture of the product of Example V (147 mg; 0.390 mmole) and 45 mg. of 5% palladium on carbon in 20 ml. of absolute methanol was stirred under 1 atmosphere of hydrogen for 2.0 hours at room temperature. The reaction was then filtered through a pad of Celite and concentrated. Purification of the crude product by silical gel chromatography (Mallinckrodt CC-4) using mixtures of methanol in chloroform as eluents afforded the desired 4α-hydroxy-3β-(3α-hydroxyoct-1-yl)-2α-[6-(tetrazol-5-yl)hex-1-yl]cyclopentanone as a colorless oil weighing 47 mg.

The mass spectrum of the product exhibited a peak at mle 362 for M—$H_2O$. The ir spectrum of the product exhibited a strong absorption at 1,740 cm$^{-1}$ for the ketone carbonyl and no absorption at 970 cm$^{-1}$ for the trans olefin.

EXAMPLE VB

A heterogeneous mixture of 148 mg. (0.400 mmole) of the product of Example V and 45 mg. of 5% palladium on carbon in 15 ml. of absolute methanol was stirred under 1 atmosphere a 0° for 2.0 hours (one equivalent of hydrogen was consumed). The reaction was then filtered through a pad of Celite and concentrated. Purification of the crude product using mixtures of methanol in ethyl acetate afforded the desired 4α-hydroxy-3β-(3α-hydroxy-trans-1-octen-1-yl)-2α-[6-(tetrazol-5-yl)hex-1-yl]-cyclopentanone as a viscous, colorless oil weighing 22 mg.

The nmr spectrum ($CD_3OD$) of the product exhibited a multiplet at 5.72-5.51 δ for the trans olefin, a multiplet at 4.19-3.80 δ for the C$\underline{H}$O, a triplet at 2.93 δ (J = 7 cps) for the C$\underline{H}_2$-tet, and multiplets at 2.76-0.60 δ for the remaining protons.

This prostaglandin analog may be converted by the process of Example IX to 2-descarboxy-2-(tetrazol-5-yl)$PGA_1$ and by the process of Example XXIII to 2-descarboxy-2-(tetrazol-5-yl)$PGF_{1\beta}$.

EXAMPLE VI

A mixture of the bis THP ether produced in Example II (198 mg.), a 5% palladium on carbon (200 mg.) and methanol (10 ml.) was stirred under one atmosphere of hydrogen for 65 hours at room temperature. The mixture was filtered and the filtrate was concentrated (aspirator pressure, ca. 40°) to give 132 mg. of a thick, colorless oil 3β-[3α-(tetrahydropyran-2-yloxy)oct-1-yl]-2α-[6-(tetrazol-5-yl)-hex-1-yl]-4α-(tetrahydropyran-2-yloxy)cyclopentan-1α-ol. The thin layer chromatogram of the product showed a single spot which was not distinguishable from that of the starting material (from Example II) as described above. The product was identified by a hydrolysis experiment in which the $R_f$ of the hydrolyzed product was found to be 0.20 while the $R_f$ of the hydrolysis product of the starting material was 0.13.

EXAMPLE VII

A sample of the product of Example VI (21 mg.) was hydrolyzed with acetic acid (0.5 ml.) and water (0.3 ml.) and then purified as described in Example III to give pure 3β-(3α-hydroxyoct-1-yl)-2α-[6-(tetrazol-5-yl)hex-1-yl]cyclopentane-1α,4α-diol as a thick, colorless oil (8 mg.).

Thin layer chromatography of the product on silica gel glass plates developed with benzene-tetrahydrofuran-formic acid (15:5:2) exhibited a single spot (vanillin-phosphoric acid indicator) with an $R_f$ of 0.20. This product is 2-descarboxy-2-(tetrazol-5-yl)-13,14-dihydro $PGF_{1\alpha}$.

EXAMPLE VIII

The product of Example VI (131 mg.) was oxidized with Jones' reagent (0.094 ml.) was described above in Example V. Isolation of the product and subsequent hydrolysis yielded the pure product 4α-hydroxy-3β-(3α-hydroxyoct-1-yl)-2α-[6-(tetrazol-5-yl)hex-1-yl]cyclopentanone as a thick, clear, colorless oil (49 mg.). Thin layer chromatography of the product on silica gel glass plates developed with methylene chloride-methanol (9:1) showed a single spot (vanillin-phosphoric acid indicator) with an $R_f$ 0.31. The infrared spectrum ($CHCl_3$) of the product showed a strong absorption band at 1,730 cm$^{-1}$ (C=O) and a moderately weak bond a 3,610 cm$^{-1}$ (OH). This product is 2-descarboxy-2-(tetrazol-5-yl)-13,14-dihydro $PGE_1$. The uv spectrum (95% EtOH) of the product exhibited only end absorption, and treatment of the uv spectrum sample with 40% potassium hydroxide did not form a product(s) with significant absorption maxima in the 220–300 mμ region of the spectrum.

This prostaglandin analog may be converted by the process of Example IX to 4β(3α-hydroxyoct-1-yl)-5α-[6-(tetrazol-5-yl)hex-1-yl]cyclopent-2-en-1-one, 2-descarboxy-2-(tetrazol-5-yl)-13,14-dihydro $PGA_1$ and by the process of Example XXIII to 2-descarboxy-2-(tetrazol-5-yl)-13,14-dihydro $PGF_{1\beta}$.

EXAMPLE IX

The product of Example V (45 mg.) was stirred with 97% formic acid (0.18 ml.) for 2½ hours. The resulting mixture was diluted with ice-water (ca. 4 ml.). The aqueous mixture was extracted with three 5-ml. portions of ethyl acetate. The extract was dried ($Na_2SO_4$) and concentrated (aspirator pressure, ca. 40°–50°) to give a crude oil (39 mg.). Chromatography of the crude product on acidic silica gel (4 g., Malinckrodt CC-4, 100-200 mesh) using mixtures of chloroform and methanol as the eluent to separate the desired product 4β-(3α-hydroxy-trans-1-octen-1-yl)-5α-[6-(tetrazol-5-yl)-cis-2-hexen-1-yl]cyclopent-2-en-1-one, as a thick, colorless oil (10 mg.) and an unidentified product (17 mg.). Thin layer chromatography of the product on silica gel glass plates developed with benzene-tetrahydrofuran-formic acid (15:5:2) showed a single spot (vanillin-phosphoric acid indicator) with an $R_f$ 0.50. The infrared spectrum (CHCl$_3$) of the product showed a strong absorption band at 1,710 cm$^{-1}$ (conjugated C=O in a five-membered ring) and a moderately weak band at 3,610 cm$^{-1}$ (OH). The uv spectrum (95% EtOH) of the product exhibited an absorption maximum at 222 mμ. This product is 2-descarboxy-2-(tetrazol-5-yl) $PGA_2$.

EXAMPLE X

To a solution cooled to −78° of 2.68 g. (6.00 mmoles) of 2-[3α-p-biphenylcarboxy-5α-hydroxy-2β-[3-oxo-trans-1-octen-1-yl]cyclopent-1α-yl]acetic acid, γ-lactone, a known compound (see reference for Example II), in 26 ml. of anhydrous ether (Mallinckrodt) and 20 ml. of tetrahydrofuran (distilled from lithium aluminum hydride) was added dropwise 6.5 ml. (6.00 mmoles) of a 0.92 N solution of methyllithium in ether (Alfa). After being stirred at −78° for 15 minutes the reaction was quenched by the dropwise addition of glacial acetic acid until the pH of the reaction was approximately 7. The mixture was then diluted with methylene chloride and the diluted organic solution was washed with water (1X) and with saturated brine (1X), was dried (anhydrous magnesium sulfate) and was concentrated to afford 2.71 g. of the viscous, oily epimeric alcohols (97.8% yield).

The crude product was purified by column chromatography on 108 g. of silica gel (Baker 'Analyzed' Reagent 60–200 mesh) using a mixture of benzene:ethyl acetate as eluent. After elution of higher $R_f$ impurities, the desired 15α-hydroxy-15β-methyl epimer, 2-[3α-p-biphenylcarboxy-5α-hydroxy-2β-[3α-hydroxy-3β-methyl-trans-1-octen-1-yl]cyclopent-1α-yl]acetic acid, ε-lactone was eluted weighing 0.853 g. (30.8% yield). Thin layer chromatography of the product on silica gel glass plates using a 10:1 mixture of ether:2-butanone as eluent showed a single spot having an $R_f = 0.45$.

The ir spectrum (CHCl$_3$) of the product exhibited strong absorptions at 1,710 cm$^{-1}$ for the ester carbonyl and 1,770 cm$^{-1}$ for the lactone carbonyl. The nmr spectrum (CDCl$_3$) of the product showed a multiplet at 7.28–8.22 δ for the aromatic protons, a multiplet at 5.56–5.77 δ for the olefinic protons, a multiplet at 4.90–5.45 δ for the —CHOCO—, a singlet at 1.27 δ (—CH$_3$), and multiplets at 0.57–3.10 δ for the remaining protons.

The above product may be reduced according to the procedure of Example XXXII to provide 2-[2β-(3β-methyl-3α-hydroxy-trans-1-octen-1-yl)-3α,5α-dihydroxycyclopent-1α-yl]acetaldehyde, γ-hemiacetal. This compound may be converted according to the procedure of Example XXXIII to 15-methyl-2-descarboxy-2-(tetrazol-5-yl)PGF$_{2\alpha}$.

EXAMPLE XI

A heterogeneous mixture of 1.30 g. (2.81 mmoles) of the chromatographed ester of Example X, 25 ml. of methanol, and 0.388 g (2.81 mmoles) finely powdered anhydrous potassium carbonate was stirred under nitrogen for 2.0 hours at room temperature then was cooled in ice. To the cooled solution was added 5.60 ml. (5.60 mmoles) of 1.0 N hydrochloric acid. The cold, acidified solution was stirred for 10 minutes then was diluted with 25 ml. of saturated brine. After filtration of the resultant solids the filtrate was extracted with ethyl acetate (3X). The cmbined ethyl acetate extracts were washed with water (1X), were dried (anhydrous magnesium sulfate), and were concentrated to afford 0.744 g. (94.0% yield) of a yellow, oily diol, 2-[3α,5α-dihydroxy-2β-(3α-hydroxy-3β-methyl-trans-1-octen-1-yl)cyclopent-1α-yl]acetic acid, γ-lactone.

This oil was purified by column chromatography on silica gel (Baker 'Analyzed' Roagent 60-200 mesh) using a 1:1 mixture of methylene chloride: ethyl acetate as eluent. After elution of higher $R_f$ impurities 0.507 g. of the desired diol was collected (64.0% yield). Thin layer chromatography of the diol product on silica gel glass plates using a 9:1 mixture of methylene chloride:methanol as eluent showed a single spot having an $R_f = 0.65$.

The ir spectrum (CHCl$_3$) of the diol exhibited a strong absorption at 1,770 cm$^{-1}$ for the lactone carbonyl. The nmr spectrum (CDCl$_3$) of the diol product exhibited a multiplet at 5.46–5.70 δ for the olefinic protons, a multiple at 4.75–5.14 δ for the HO-CH, a multiplet at 3.75–4.21 δ for the HCOCO-, a singlet at 1.26 δ for the —CH$_3$, and multiplets at 0.68–3.11 δ for the remaining protons.

EXAMPLE XII

To a solution, cooled in ice, of 0.507 g. (1.80 mmole) of the chromatographed diol of Example XI in 5.4 ml. of methylene chloride was added 0.54 ml. of dihydropyran (distilled from lithium aluminum hydride), and 18 mg. of p-toluenesulfonic acid monohydrate. The solution was stirred in the cold for 15 minutes then was diluted with ether. The organic solution was washed with saturated sodium bicarbonate (1X), was dried (anhydrous magnesium sulfate), and was concentrated to afford 0.870 g. (107% yield) of the pale-yellow, oily bis-THP ether 2-[5α-hydroxy-3α-(tetrahydropyran-2-yloxy)-2β-(3β-methyl-3α-(tetrahydropyran-2-yloxy)-trans-1-octen-1-yl)cyclopent-1α-yl]acetic acid, γ-lactone, which was used without further purification. Thin layer chromatography of the oily product on silica gel glass plates using 5% methanol in methylene chloride as eluent showed a single spot having an $R_f = 0.85$. The structure of the product was substantiated by the virtual identity of its ir spectrum with that of the known 15-normethyl compound (see reference for Example II).

The above product may be hydrogenated according to the procedure of Example VA to provide 2-[5α-hydroxy-3α-(tetrahydropyran-2-yloxy)-2β-(3β-methyl-3α-(tetrahydropyran-2-yloxy)oct-1-yl)cyclopent-1α-yl]acetic acid, γ-lactone.

This product may be reduced according to the procedure of Example XIII to afford 2-[5α-hydroxy-3α-(tetrahydropyran-2-yloxy)-2β-(3β-methyl-3α-(tetrahydropyran-2-yloxy)oct-1-yl)cyclopent-1α-yl]acetaldehyde, γ-hemiacetal, a compound necessary for the preparation of 15-methyl-2-descarboxy-2-(tetrazol-5-yl)-13,14-dihydro PGF$_{2\alpha}$, PGF$_{2\beta}$, PGE$_2$ and PGA$_2$.

EXAMPLE XIII

To a solution cooled to −78° of 0.810 g. (1.80 mmoles) of the crude bis-THP ether lactone of Example XII in toluene was added 2.3 ml. (1.85 mmoles) of a 0.805 M solution of diisobutylaluminum hydride in hexane (Alfa). The solution was stirred at −78° for 15 minutes then was quenched by the dropwise addition of methanol until gas evolution ceased. The quenched mixture was warmed to room temperature then was concentrated. The resultant oil was dissolved in ether and the ethereal solution was washed with a 50% sodium potassium tartrate solution (2X) and with saturated brine (1X), was dried (anhydrous magnesium sulfate), and was concentrated to afford 0.800 g. (98.5% yield) of the oily hemiacetal 2-[5α-hydroxy-3α-(tetrahydropyran-2-yloxy)-2β-(3β-methyl-3α(tetrahydropyran-2-yloxy)-trans-1-octen-1-yl)cyclopent-1α-yl]acetaldehyde, γ-hemiacetal.

The oil was purified by column chromatography on silica gel (Baker 'Analyzed' Reagent (60–200 mesh) using first benzene as eluent to remove high $R_f$ impurities than a 2:1 mixture of benzene:ethyl acetate to elute the colorless, oily product weighing 0.601 g. (74.0% yield). Thin layer chromatography of the oily product on silica gel glass plates using a 4:1 mixture of benzene:ethyl acetate as eluent showed a single spot having an $R_f = 0.10$. The structure was confirmed by the virtual identity of its ir spectrum with that of the known 15-normethyl compound (see reference for Example II).

EXAMPLE XIV

To a solution of 0.985 g. (2.08 mmoles) of the bromide of Example I in 1.94 ml. of dimethyl sulfoxide was added dropwise 2.38 ml. (5.24 mmoles) of a 2.2 M sodium methylsulfinylmethide solution. To the resultant red ylide solution was added dropwise over a 20 minute period a solution of 0.375 g. (0.83 mmole) of the chromatographed hemiacetal of Example XIII in 1.66 ml. of dimethyl sulfoxide. The solution was stirred for an additional 2.5 hours then was poured onto 50 ml. of ice water. The aqueous solution was acidified to pH 3 with 10% hydrochloric acid. The aqueous layer was then extracted with ethyl acetate (5X); the combined organic extracts were dried (anhydrous magnesium sulfate) and were concentrated to afford and oil weighing 0.987 g.

This oil was purified by column chromatography on 40 g. of silica gel (Baker 'Analyzed' Reagent 60–200 mesh) using 10% ethyl acetate in chloroform as eluent. After elution of higher $R_f$ impurities, 185 mg. (49.4% yield) of starting hemiacetal were recovered. Further elution afforded 90 mg. (26.9% yield based on unrecovered starting hemiacetal of the oily product 1α-hydroxy-4α-(tetrahydropyran-2-yloxy)-3β-[3β-methyl-3α-(tetrahydropyran-2-yloxy)-trans-1-octen-1-yl]-2α-[6-(tetrazol-5-yl)-cis-2-hexen-1-yl]cyclopentane (herein called compound A). Thin layer chromatography of the oily product on silica gel glass plates using 10% methanol in methylene chloride as eluent showed a single spot having an $R_f = 0.40$.

The structure of the product was confirmed by the virtual identity of its ir spectrum with that of the 15-normethyl compound (see Example II).

The above compound A may be converted by the process of Example VI to 1α-hydroxy-3β-[3β-methyl-3α-(tetrahydropyran-2-yloxy)oct-1-yl]-2α-[6-(tetrazol-5yl)hex-1-yl]-4α-(tetrahydropyran-2-ylaxy)cyclopentane, an intermediate which can be converted by the process of Example VII to 1α,4α-dihydroxy-3β-(3α-hydroxy-3β-methyloct-1-yl)-2α-[6-(tetrazol-5-yl)hex-1-yl]cyclopentane, 2-descarboxy-2-(tetrazol-5-yl)-15-methyl-13,14-dihydro $PGF_{1\alpha}$ or by the process of Example XIV above to 4α-(tetrahydropyran-2-yloxy)-3β-[3β-methyl-3α-(tetrahydropyran-2-yloxy)oct-1-yl]-2α-[6-(tetrazol-5yl)hex-1-yl]cyclopentanone, another important intermediate.

This last named intermediate may be converted by the process of Example XVII to 4α-hydroxy-3β-[3α-hydroxy-3β-methyloct-1-yl]2α-[6-(tetrazol-5yl)hex-1-yl]cyclopentanone, 2-descarboxy-2-(tetrazol-5-yl)-15-methyl-13,14-dihydro $PGE_1$.

The 2-descarboxy-2-(tetrazol-5-yl)-15-methyl-13,14-dihydro-$PGE_1$ may be converted by the method of Example IX to 4β-[3α-hydroxy-3β-methyloct-1-yl]-5α-[6-(tetrazol-5-yl)hex-1-yl]cyclopent-2-en-1-one, 2-descarboxy-2-(tetrazol-5-yl)-15-methyl-13,14-dihydro $PGA_1$.

The 2-descarboxy-2-(tetrazol-5-yl)-15-methyl-13,14-dihydro-$PGE_1$ may be converted by the method of Example XXIII to 2-descarboxy-2-(tetrazol-5-yl)-15-methyl-13,14-dihydro $PGF_{1\beta}$.

The important intermediate compound A may also be converted by a modified process of Example VI wherein the reaction temperature is −20° to 1-hydroxy-4α-(tetrahydroptran-2-yloxy)-3β-[3β-methyl-3α-(tetrahydropyran-2-yloxy)-trans-1-octen-1yl]-2α-[6-(tetrazol-5yl-hex-1-yl]cyclopentane, (herein called compound B). Compound B may be converted by the process of Example XV to 1α,4α-dihydroxy-3β-[3α-hydroxy-3β-methyl-trans-1-octenyl]-2α-[6-(tetrazol-5-yl)-hex-1-yl]cyclopentane, 2-descarboxy-2-(tetrazol-5-yl)-15-methyl $PGF_{1\alpha}$.

Compound B above may be converted by the process of Example XIV to 4α(tetrahydropyran-2-yloxy)-3β-[3β-methyl-3α-(tetrahydropyran-2-yloxy)-trans-1-octen-1-yl]-2α-[6-(tetrazol-5-yl)-hex-1-yl]cyclopentanone, another important intermediate, which may be further converted by the process of Example XVII to 4α-hydroxy-3β-[3α-hydroxy-3β-methyl-trans-1-octen-1-yl]-2α-[6-(tetrazol-5-yl)-hex-1-yl]cyclopentanone, 2-descarboxy-2-(tetrazol-5-yl)-15-methyl $PGE_1$.

The tetrazoyl analog of 15-methyl $PGE_1$ may be converted by the process of Example IX to 4β-(3α-hydroxy-3β-methyl-trans-1-octen-1-yl)-5α-[6-(tetrazol-5-yl)-hex-1-yl]cyclopent-2-ene-1-one, the 2-descarboxy-2-(tetrazol-5-yl)-15-methyl $PGA_1$.

The tetrazoyl analog of 15-methyl $PGE_1$ may be converted by the process of Example XXIII to the 2-descarboxy-2-(tetrazol-5-yl)-15-methyl $PGF_{1\beta}$.

EXAMPLE XV

A solution of 8.0 mg. of the bis-THP ether of Example XIV in 0.40 ml. of a 65.35 mixture of acetic acid:-water was stirred at 40° for 5.0 hours then was concentrated by rotary evaporation. The crude oil was purified by column chromatography on silica gel (Mallinckrodt CC-4) using 5% methanol in chloroform as eluent. A 3.5-mg. portion of the oily triol, 1α,4α-dihydroxy-3β-[3α-hydroxy-3β-methyl-trans-1-octen-1-yl]-2α-[6-(tetrazol-5-yl)-cis-2-hexen-1-yl]cyclopentane was obtained.

The structure of the oily triol was substantiated by the virtual identity of its ir spectrum with that of the known 15-normethyl compound (see Example III). This compound is the 2-descarboxy-2-(tetrazol-5-yl)-15-methyl $PGF_{2\alpha}$.

EXAMPLE XVI

To a solution cooled to −15° of 105 mg. (0.187 mmole) of the chromatographed bis-THP ether of Example XIV in 2.0 ml. of acetone was added dropwise 0.1 ml. of Jones reagent. The mixture was stirred for 30 minutes in the cold then was quenched by the addition of 0.5 ml. of 2-propanol. The solution was diluted with ethyl acetate, then was washed with water (2X) and saturated brine (1X), was dried (anhydrous magnesium sulfate), and was concentrated to afford 82 mg. (78% yield) of an oily ketone. The crude oil was purified by column chromatography on silica gel (Baker 'Analyzed' Reagent 60–200 mesh) using 10% ethyl acetate in chloroform as eluent which afforded 56 mg. (53.4% yield) of purified oily ketone 4α-(tetrahydropyran-2-yloxy)-3β-[3β-methyl-3α-(tetrahydropyran-2-yloxy)-trans-1-octen-1-yl]-2α-[6-(tetrazol-5-yl)-cis-2-hexen-1-yl]cyclopentanone. Thin layer chromatography of the oily product on silica gel glass plates using 10% methanol in methylene chloride as eluent showed a single spot having an $R_f = 0.55$.

The structure was confirmed by the virtual identity of its ir spectrum with that of the 15-normethyl compound (see Example IV).

EXAMPLE XVII

A solution of 57 mg. (0.10 mmole) of the chromatographed bis-THP ether of Example XVI in 0.88 ml. of a 65:35 mixture of acetic acid:water was stirred at 42° for 4.0 hours then was concentrated by rotary evaporation. Chromatography of the crude product weighing 48 mg. on silica gel (Mallinckrodt CC-4) using 2% methanol in chloroform as eluent afforded 13 mg. (33.4% yield) of oily 4α-hydroxy-3β-[3α-hydroxy-3β-methyl-trans-1-octen-1-yl]-2α-[6-(tetrazol-5-yl)-cis-2-hexen-1-yl]cyclopentanone. This compound is the 2- descarboxy-2-(tetrazol-5-yl)-15-methyl PGE$_2$.

The structure was substantiated by the practical identity of its ir spectrum to that of the 15-normethyl compound. Treatment of a methanolic solution of the oily product with 40% aqueous potassium hydroxide afforded the expected uv absorption at 278 m$\mu$ ($\epsilon$ 20,000).

The tetrazoyl analog of 15-methyl PGE$_2$ may be converted by the process of Example IX to 4$\beta$-(3$\alpha$-hydroxy-3$\beta$-methyl-trans-1-octen-1-yl)-5$\alpha$-[6-(tetrazol-5-yl)-cis-2-hexen-1-yl]cyclopent-2-ene-1-one, the 2-descarboxy-2-(tetrazol-5-yl)-15-methyl PGA$_2$.

The tetrazoyl analog of 15-methyl PGE$_2$ may be converted by the process of Example XXIII to the 2-descarboxy-2-(tetrazol-5-yl)-15-methyl PGF$_{2\beta}$.

EXAMPLE XVIII

A mixture of the chromatographed bis-THP ether of Example II (130 mg., 0.23 mmole), 5% palladium on carbon (32.5 mg.), and methanol (13 ml.) is stirred magnetically under one atmosphere of hydrogen at $-15°$ to $-20°$C. for 3.0 hours. The resulting mixture is filtered through Celite 545, and the filtrate is concentrated (ca. 30°–40°, aspirator pressure) to afford the colorless, oily 1$\alpha$-hydroxy-4$\alpha$-(tetrahydropyran-2-yloxy)-3$\beta$-[3$\alpha$-(tetrahydropyran-2-yloxy)-trans-1-octen-1-yl]-2$\alpha$-[6-(tetrazol-5-yl)-hex-1-yl]cyclopentane (herein called Compound C).

This compound C may be converted by the process of Example III to 3$\beta$-(3$\alpha$-hydroxy-trans-1-octen-1-yl)-2$\alpha$-[6-(tetrazol-5-yl)hex-1-yl]cyclopentan-1$\alpha$,4$\alpha$-diol, the 2-descarboxy-2-(tetrazol-5-yl) PGF$_{1\alpha}$.

Compound C above may also be converted by the processes of Examples IV and V to 4$\alpha$-hydroxy-3$\beta$-(3$\alpha$-hydroxy-trans-1-octen-1-yl)-2$\alpha$-[6-(tetrazol-5-yl)hex-1-yl]cyclopentanone, the 2-descarboxy-2-(tetrazol-5-yl) PGE$_1$.

The tetrazoyl analog of PGE$_1$ may be converted by the process of Example IX to 4$\beta$-(3$\alpha$-hydroxy-trans-1-octen-1-yl)-5$\alpha$-[6-(tetrazol-5-yl)hex-1-yl]cyclopent-2-en-1-one, the 2-descarboxy-2-(tetrazol-5-yl) PGA$_1$.

The tetrazoyl analog of PGE$_1$ may be converted by the process of Example XXIII to the 2-descarboxy-2-(tetrazol-5-yl) PGF$_{1\beta}$.

EXAMPLE XIX

A mixture of the known 2-[5$\alpha$-hydroxy-3$\alpha$-(tetrahydropyran-2-yloxy)-2$\beta$-(3$\alpha$-(tetrahydropyran-2-yloxy)-trans-1-octen-1yl)-cyclopentan-1$\alpha$-yl]acetic acid, $\gamma$-lactone (0.840 g., 1.92 mmoles), 5% palladium on carbon (0.10 g.) and absolute ethanol (25 ml.) is stirred magnetically under 1 atmosphere of hydrogen at room temperature for 5 hours. The resulting mixture is filtered, and the filtrate is concentrated to afford a thick, colorless oil, 2-[5$\alpha$-hydroxy-3$\alpha$-(tetrahydropyran-2-yloxy)-2$\beta$-(3$\alpha$-(tetrahydropyran-2-yloxy)oct-1-yl)cyclopentan-1$\alpha$-yl]acetic acid, $\gamma$-lactone. The compound is converted by the method of Example XIII to 2-[5$\alpha$-hydroxy-3$\alpha$-(tetrahydropyran-2-yloxy)-2$\beta$-(3$\alpha$-(tetrahydropyran-2-yloxy)oct-1-yl)cyclopentan-1$\alpha$-yl]acetaldehyde, $\gamma$-hemiacetal.

This compound is converted by the method of Example II to 3$\beta$-[3$\alpha$-(tetrahydropyran-2-yloxy)oct-1-yl]-2$\alpha$-[6-(tetrazol-5-yl)cis-2-hexen-1-yl]-4$\alpha$-(tetrahydropyran-2-yloxy)cyclopentanol (herein called compound D).

Compound D may be converted by the process of Example III tp 3$\beta$-(3$\alpha$-hydroxyoct-1-yl)-2$\alpha$-[6-(tetrazol-5-yl)-cis-2-hexen-1-yl]cyclopentan-1$\alpha$,4$\alpha$-diol, the 2-descarboxy-2-(tetrazol-5-yl)-13,14-dihydro PGF$_{2\alpha}$.

Compound D may be converted by the process of Examples IV and V to 4$\alpha$-hydroxy-3$\beta$-(3$\alpha$-hydroxyoct-1-yl)-2$\alpha$-[6-(tetrazol-5-yl)-cis-2-hexen-1-yl]-cyclopentanone, 2-descarboxy-2-(tetrazol-5-yl)-13,14-dihydro PGE$_2$.

The tetrazoyl analog of 13,14-dihydro PGE$_2$ may be converted by the process of Example IX to 4$\beta$-(3$\alpha$-hydroxyoct-1-yl)-5$\alpha$-[6-(tetrazol-5yl)-cis-2-hexen-1-yl]cyclopent-2-en-1-one, the 2-descarboxy-2-(tetrazol-5-yl)-13,14-dihydro PGA$_2$.

The tetrazoyl analog of 13,14-dihydro PGE$_2$ may be converted by the process of Example XXIII to the 2-descarboxy-2-(tetrazol-5-yl)-13,14-dihydro PGF$_{2\beta}$.

EXAMPLE XX

A mixture of 2.68 g. (6.00 mmoles) of the $\gamma$-lactone starting material of Example X and 0.636 g. of 10% palladium on carbon in 29 ml. of absolute ethanol was stirred under 1 atmosphere of hydrogen at ambient temperature for 5 hours, then the mixture was filtered through Celite 545. Concentration of the filtrate afforded the desired 2-[3$\alpha$-p-biphenylcarboxy-5$\alpha$-hydroxy-2$\beta$-[3-oxooct-1-yl]cyclopent-1$\alpha$-yl]acetic acid, $\gamma$-lactone.

This compound may be converted by the process of Example X to 2-[3$\alpha$-p-biphenylcarboxy-5$\alpha$-hydroxy-2$\beta$-[3$\alpha$-hydroxy-3$\beta$-methyloct-1-yl]cyclopent-1$\alpha$-yl]acetic acid, $\gamma$lactone, which may be converted by the process of Example XI to 2-[3$\alpha$,5$\alpha$-dihydroxy-2$\beta$-(3$\alpha$-hydroxy-3$\beta$-methyloct-1-yl)cyclopent-1$\alpha$-yl]acetic acid, $\gamma$-lactone.

The latter compound may be converted by the process of Example XII to 2-[5$\alpha$-hydroxy-3$\alpha$-(tetrahydropyran-2-yloxy)-2$\beta$-(3$\beta$-methyl-3$\alpha$-(tetrahydropyran-2-yloxy)oct-1-yl)cyclopentan-1$\alpha$-yl]acetic acid, $\gamma$-lactone which may be converted by the process of Example XIII to 2-[5$\alpha$-hydroxy-3$\alpha$-(tetrahydropyran-2-yloxy)-2$\beta$-(3$\beta$-methyl-3$\alpha$-(tetrahydropyran-2-yloxy)oct-1-yl)cyclopent-1$\alpha$-yl]acetaldehyde, $\gamma$hemiacetal.

The latter compound may be converted by the process of Example XIV to 1$\alpha$-hydroxy-4$\alpha$-(tetrahydropyran-2-yloxy)-3$\beta$-[3$\beta$-methyl-3$\alpha$-(tetrahydropyran-2-yloxy) oct-1-yl]-2$\alpha$-[6-(tetrazol-5-yl)-cis-2-hexen-1-yl]cyclopentane (herein called compound E), an important intermediate in the synthesis of 13,14-dihydro-15-lower alkyl tetrazoyl analogs of prostaglandins.

Compound E is converted by the process of Example XV to 1$\alpha$,4$\alpha$-dihydroxy-3$\beta$-[3$\alpha$-hydroxy-3$\beta$-methyloct-1-yl]-2$\alpha$-[6-(tetrazol-5-yl)-cis-2-hexen-1-yl]-cyclopentane, the 2-descarboxy-2-(tetrazol-5-yl)-13,14-dihydro-15-methyl PGF$_{2\alpha}$.

Compound E above may be converted by the process of Example XVI to 4$\alpha$-(tetrahydropyran-2-yloxy)-3$\beta$-[3$\beta$-methyl-3$\alpha$-(tetrahydropyran-2-yloxy)oct-1-yl]-2$\alpha$-[6-(tetrazol-5-yl)-cis-2-hexen-1-yl]cyclopentanone, an intermediate, which may be further converted by the process of Example XVII to 4$\alpha$-hydroxy-3$\beta$-[3$\alpha$-hydroxy-3$\beta$-methyloct-1-yl]-2$\alpha$-[6-(tetrazol-5-yl)-cis-2-hexen-1-yl]-cyclopentanone, the 2-descarboxy-2-(tetrazol-5-yl)-13,14-dihydro-15-methyl PGE$_2$.

The latter prostaglandin analog may be converted by the process of Example IX to 4$\beta$-[3$\alpha$-hydroxy3$\beta$-methyloct-1yl]-5$\alpha$-[6-(tetrazol-5-yl)-cis-2-hexen-1-yl]cyclopent-2-en-1-one, the 2-descarboxy-2-(tetrazol-5-yl)-13,14-dihydro-15-methyl PGA$_2$.

The 2-descarboxy-2-(tetrazol-5-yl)-13,14-dihydro-15-methyl PGE$_2$ analog may be converted by the process of Example XXIII to the 2-descarboxy-2-(tetrazol-5-yl)-13,14-dihydro-15-methyl PGF$_{2\beta}$.

EXAMPLE XXI

The known compound 2-[5α-hydroxy-3α-(tetrahydropyran-2-yloxy)-2β-(3α-(tetrahydropyran-2yloxy)-cis-5-trans-1octadien-1-yl)cyclopent-1α-yl] acetaldheyde, γ-hemiacetal (see E. J. Corey, et al., J. Amer. Chem. Soc., 93, 1490 (1971) may be converted by the process of Example XI to 1α-hydroxy-3β-[3α-(tetrahydropyran-2-yloxy)-trans1-cis-5-octadien-1-yl]-2α-[6-(tetrazol-5-yl) cis-2-hexen-1-yl]-4α-(tetrahydropyran-2-yloxy)cyclopentanne, an important intermediate in the synthesis of tetrazoyl analogs of the PG$_3$ series, herein called compound F.

Compound F may be, converted by the process of Example III to 3β-(3α-hydroxy-trans-1-cis-5-octadien-1-yl)-2α-[6-(tetrazol-5-yl)-cis-2-hexen-1-yl]-cyclopentan-1α,4α-diol, the 2-descarboxy-2-tetrazol-5-yl) PGF$_{3\alpha}$.

Compound F above may be converted by the process of Example IV to 4α-(tetrahydropyran-2-yloxy)-3β-[3α-(tetrahydropyran-2-yloxy)-trans-1-cis-5-octadien-1-yl]cyclopentanone, an intermediate which may be converted by the process of Example V to 4α-hydroxy-3β-(3α-hydroxy-trans-1-cis-5-octadien-1-yl)-2α-[6-(tetrazol-5-yl)-cis-2-hexen-1-yl]cyclopentanone, the 2-descarboxy-2-(tetrazol-5-yl) PGE$_3$.

The latter prostaglandin analog may be converted by the process of Example IX to 4β-(3α-hydroxy-trans-1-cis-5-octadien-1-yl)-5α-[6-(tetrazol-5-yl-cis-2-hexen-1-yl]cyclopent-2-en-1-one, the 2-descarboxy-2-(tetrazol-5-yl) PGA$_3$.

EXAMPLE XXII

To a solution of 58 mg (0.154 mmole) of the 2-descarboxy-2-(tetrazol-5-yl)PGE$_2$ prepared in Example V in 5 ml. of ethyl acetate was added dropwise a solution of diazomethane in ether (ca. 0.3 ml prepared from N-methyl-N'-nitro-N-nitrosoguanidine according to the procedure found in Fieser and Fieser, "Reagents for Organic Synthesis," Volume I, page 192). The yellow solution was stirred for 5 minutes then was concentrated by rotary evaporation to afford a clear tan oil. Purification of the crude product by column chromatography (Baker "Analyzed" silica gel 60–200 mesh) using mixtures of methanol in chloroform afforded 29 mg. of 2-descarboxy-2-(2-N-methyltetrazol-5-yl)PGE$_2$ and 7 mg. of 2-descarboxy-2-(1-N-methyltetrazol-5-yl)PGE$_2$.

The ir spectra (CHCl$_3$) of both products were superimposable exhibiting strong absorbances at 1,740 cm$^{-1}$ (C = 0) and 965 cm$^{-1}$ (trans olefin).

The uv spectra (EtOH) of both products after treatment with KOH showed a $\lambda_{max}$ at 278 nm with an $\epsilon$ = 23,500.

EXAMPLE XXIII to a solution, cooled in ice, of 35 mg of the 2-descarboxy-2-(tetrazol-5-yl(PGE$_2$ prepared in Example V in 7 ml. of absolute methanol was added an ice-chilled solutin of 105 mg. of sodium borohydride in 12 ml. of absolute methanol. The solution was stirred under nitrogen for 20 minutes at 0°–5° then for 1.0 hour at room temperature. The reaction mixture was then cooled in ice, 2 ml. of water was added, and the resultant solution was concentrate The concentrated mixture was overlaid with ethyl acetate, was acidified with 10% hydrochloric acid, and the acidified aqueous layer was extracted with ethyl acetate (4 × 5 ml.). The combined extracts were washed with water and saturated brine, were dried (anhydrous magnesium sulfate), and were concentrated. The crude residue was purified by column chromatography (Mallinckrodt CC-7) using mixtures of methanol in methylene chloride as eluents to afford first 2-descarboxy-2-(tetrazol-5-yl)PGF$_{2\alpha}$ then 2-descarboxy-2-(tetrazol-5-yl)PGF$_{2\beta}$ as viscous, colorless oils. The ir spectra (CHCl$_3$) of the two products were superimposable.

EXAMPLE XXIV

A heterogeneous mixture of 2.24 g. (5.0 mmoles) of the known (E. J. Corey, et al., JACS, 93, 1491 (1971) 2-[5α-hydroxy-3α-p-phenylbenzoyloxy-2β-(3β-hydroxy-trans-octen-1-yl)cyclopent-1α-yl]acetic acid, γ-lactone and 0.680 g (5.0 mmoles) of anhydrous potassiuum carbonate in 22 ml. of absolute methanol was stirred at room temperature under nitrogen for 2.0 hours. The reaction mixture was then cooled in ice and was quenched by the addition of 10 ml. of 1.0N aqueous hydrochloric acid. The quenched mixture was diluted with water (22 ml.) and filtered to remove the precipitated methyl p-phenylbenzoate. The filtrate was extracted with ethyl acetate (3 × 5 ml.); the combined organic extracts were washed with saturated sodium bicarbonate and saturated brine, were dried (anhydrous magnesium sulfate), and were concentrated to afford the desired 2-[3α,5α-dihydroxy-2β-(3β-hydroxy-trans-1-octen-1-yl)cyclopent-1α-yl]-acetic acid, γ-lactone as a viscous oil weighing 1.17 g. (87.4% yield). The ir and nmr spectra of the product were superimposable on those of the known 15α-epimer.

The starting material above may be reduced by the procedure of Example XXXII to the 2-[2β-(3β-hydroxy-trans-1-octen-1-yl)-3α,5α-dihydroxycyclopent-1αyl]acetaldehyde, γ-hemiacetal.

This material may be converted by the procedure of Example XXXIII to the 15-epi-2-descarboxy-2-(tetrazol-5-yl) PGF$_{2\alpha}$.

The starting material above may be hydrogenated according to the procedure of Example XXXIV to the 2-[3α-pphenylbenzoyloxy-2β-(3β-hydroxyoct-1-yl)5α-hydroxycyclopent-1α-yl]acetic acid, γ-lactone.

This compound may be reduced as described in Example XXXII to 2-[3α,5α-dihydroxy-2β-(3β-hydroxyoct-1-yl)cyclopent-1α-yl]-acetaldehyde, γ-hemiacetal.

This compound may be converted to 15-epi-2-descarboxy-2-(tetrazol-5-yl)-13,14-dihydro PGF$_{2\alpha}$ following the method of Example XXXIII.

EXAMPLE XXV

To a solution of 1.17 g. (4.37 mmoles) of the 2-[3α,-5α-dihydroxy-2β(3β-hydroxy-trans-1-octen-1-yl)cyclopent-1α-yl]acetic acid, γ-lactone prepared above in Example XXIV and 1.17 ml. of 2,3-dihydropyran in 12 ml. of methylene chloride was added 12 mg. of p-toluenesulfonic acid monohydrate. The reaction was stirred under nitrogen at room temperature for 15 minutes then was diluted with ether (100 ml.). The diluted solution was washed with saturated sodium bicarbonate and saturated brine, was dried (anhydrous magnesium sulfate), and was concentrated to afford the desired 2-[5α-hydroxy-3α-(tetrahydropyran-2-yloxy)-2β-(3β-

(tetrahydropyran-2-yloxy)-trans-octen-1-yl)cyclopent-1α-yl]acetic acid, γ-lactone as a viscous oil weighing 2.10 g. (> 100% yield). The ir and nmr spectra were superimposable on those of the known 15α-epimer.

EXAMPLE XXVI

A heterogeneous mixture of 2.02 g. of the 2-[5α-hydroxy-3α-(tetrahydropyran-2-yloxy)-2β-(3β-tetrahydropyran-2-yloxy)-trans-1-octen-1-yl)cyclopent-1α-yl]acetic acid, γ-lactone prepared above and 202 mg. of 5% palladium on carbon in 20 ml. of absolute methanol is stirred under 1 atmosphere of hydrogen for 4.5 hours at room temperature. The mixture is then filtered (Celite); concentration of the filtrate provides the desired 2-[5α-hydroxy-3α-(tetrahydropyran-2-yloxy)-2β-(3β-(tetrahydropyran-2-yloxy)oct-1-yl)-cyclopent-1α-yl]acetic acid, γ-lactone.

This compound may be reduced as follows in Example XXVII to provide the hemiacetal useful for the preparation of the 15-epi-13,14-dihydro $PGE_2$, $PGF_{2\alpha}$, $PGF_{2\beta}$, and $PGA_2$ tetrazole analogs.

EXAMPLE XXVII

To a solution, cooled to −78° under nitrogen, of 1.90 g. (4.37 mmoles) the 2-[5α-hydroxy-3α-(tetrahydropyran-2-yloxy)-2β-(3β-(tetrahydropyran-2-yloxy)-trans-octen-1-yl)cyclopent-1α-yl]-acetic acid, γ-lactone prepared above in Example XXVI in 25 ml. of dry toluene was added dropwise 5.92 ml. of a 20% solution of diisobutylaluminum hydride in hexane (Alfa Inorganics). The reaction was stirred for 45 minutes at −78° then was quenched by the dropwise addition of methanol until gas evolution ceased. The quenched reaction was let warm to room temperature, was diluted with ether, was reached with a 50% sodium potassium tartrate solution and with saturated brine, was dried (anhydrous magnesium sulfate), and was concentrated to provide a viscous, yellow oil which was purified by column chromatograhy (Baker Silica Gel 60–200 mesh) using mixtures of benzene:ethyl acetate as eluents. After removal of less polar impurities the desired 2-[5α-hydroxy-3α-(tetrahydropyran-2-yloxy)2β-(3β-(tetrahydropyran-2-yloxy)-trans-octen- 1-yl)cyclopent-1α-yl]acetaldehyde, γ-hemiacetal was collected as a colorless oil weighing 1.59 g. (83.5% yield). The ir and nmr spectra weere superimposable on those of the known 15α-epimer.

This compound may be converted into the 15-epi2-descarboxy-2-(tetrazol-5-yl) $PGE_2$, $PGF_{2\alpha}$, $PGF_{2\beta}$, $PGA_2$, $PGE_1$, $PGF_{1\alpha}$, $PGF_{1\beta}$ $PGA_1$, 13,14-dihydro $PGE_1$, $PGF_{1\alpha}$, $PGF_{1\beta}$, and $PGA_1$.

EXAMPLE XXVIII

Dimethyl 2-Oxo-undecylphosphonate:

A solution of 49.6 g. (0.40 mole) dimethyl methylphosphonate (Aldrich) in 500 ml. dry tetrahydrofuran is cooled to −78° in a dry nitrogen atmosphere. To the stirred phosphonate solution is added 188 ml. of 2.34 M n-butyllithium in hexane solution (Alfa Inorganics, Inc.) dropwise over a period of 40 minutes at such a rate that the reaction temperature never rose above −65°. After an additional 5 minutes stirring at −78°, 36.3 g. (0.20 mole) methyl decanoate is added dropwise at a rate that kept the reaction temperature less than −70° (20 minutes). After 1.0 hour at −78° the reaction mixture is allowed to warm to ambient temperature, neutralized with 25 ml. acetic acid and rotary evaporated to a white gel. The gelatinous material is taken up in 75 ml. water, the aqueous phase extracted with 100 ml. portions of chloroform (3x), the combined organic extracts are backwashed (50 cc $H_2O$), dried ($MgSO_4$), and concentrated (water aspirator) to a crude residue and distilled, to give dimethyl 2-oxo-undecylphosphonate.

This compound may be converted by methods both known (see: E. J. Corey, et al., J. Am. Chem. Soc., 92, 397 (1970) and described herein to the 2-descarboxy-2-(tetrazol-5-yl)-ω-tetrahomo $PGE_2$, $PGF_{2\alpha}$, $PGF_{2\beta}$, $PGA_2$, $PGE_1$, $PGF_{1\alpha}$, $PGF_{1\beta}$, $PGA_1$, 13,14-dihydro $PGE_2$, 13,14-dihydro $PGF_{2\alpha}$, 13,14-dihydro $PGF_{2\beta}$, 13,14-dihydro $PGA_2$, 13,14-dhydro $PGE_1$, 13,14-dihydro $PGF_{1\alpha}$, 13,14-dihydro $PGF_{1\beta}$, 13,14-dihydro $PGA_1$, the corresponding 14-epimers, and 15-lower alkyl analogs.

EXAMPLE XXIX

Dimethyl 2-Oxo-3,3-dimethylheptylphosphonate:

A solution of 18.4 g. (0.116 moles) dimethyl methylphosphonate (Aldrich) in 200 ml. dry tetrahydrofuran is cooled to −78° in a dry nitrogen atmosphere. To the stirred phosphonate solution is added 67.3 ml. of 1.90 M n-butyllithium in hexane solution (Alfa Inorganics, Inc.) dropwise over a period of 40 minutes at such a rate that the reaction temperature never rose above −65°. After an additional 5 minutes stirring at −78°, 10.2 g. (58.1 mmoles) methyl 2,2-dimethylhexanoate is added dropwise at a rate that kept the reaction temperature less than −70°(20 minutes). After 1.0 hour at −78° the reaction mixture is allowed to warm to ambient temperature, neutralized with 10 ml. acetic acid and rotary evaporated to a white gel. The gelatinous material is taken up in 75 ml. water, the aqueous phase extracted with 100 ml. portions of chloroform (3×), the combined organic extracts are backwashed (50 cc $H_2O$), dried ($MgSO_4$), and concentrated (water aspirator) to a crude residue and distilled (b.p. 80°–85° at 0.05 mm) to give dimethyl 2-oxo-3,3-dimethylheptylphosphonate.

This compound may be converted by methods both known (see: E. J. Corey, et al., J. Am. Chem. Soc., 92, 397 (1970) and described herein to the 2-descarboxy-2-(tetrazol-5-yl)-16,16-dimethyl-$PGE_2$, $PGF_{2\alpha}$, $PGF_{2\beta}$, $PGA_2$, $PGE_1$, $PGF_{1\alpha}$, $PMF_{1\beta}$, $PGA_1$, 13,14-dihydro $PGE_2$, 13,14-dihydro $PGF_{2\alpha}$, 13,14-dihydro $PGF_{2\beta}$, 13,14-dihydro $PGA_2$, 13,14-dihydro $PGE_1$, 13,14-dihydro $PGF_{1\alpha}$, 13,14-dihydro $PGF_{1\beta}$, 13,14-dihydro $PGA_1$, the corresponding 15-epimers, and 15-lower alkyl analogs.

EXAMPLE XXX

To a solution of 76 mg. (0.2 mmole) of the 2-descarboxy-2-(tetrazol-5-yl)$PGF_{2\alpha}$ prepared in Example III in 1.0 ml. of pyridine is added 120 mg. (1.0 mmole) of pivaloyl chloride. The solution is stirred for 5 hours at 45° under nitrogen then is cooled to room temperature. To the solution is then added 36 mg. (2.0 mmoles) of water. The solution is then stirred at room temperature for 2.0 hours, then is diluted with ethyl acetate. The diluted solution is washed with 0.1 N hydrochloric acid (3×), with water (1×), and with saturated brine (1×), is dried (anhydrous magnesium sulfate), and is concentrated. Purification of the crude residue by silica gel chromatography provides the desired 9α, 11α, 15α-tris-pivaloyloxy-2-descarboxy-2-(tetrazol-5-yl)$PGF_{2\alpha}$.

EXAMPLE XXXI

To a solution of 37 mg. (0.1 mmole) of 2-descarboxy-2-(tetrazol-5-yl)PGE$_2$ prepared in Example V in 0.5 ml. of dry tetrahydrofuran is added 29 mg. (0.33 mmole) of formic acetic anhydride and 35 mg. (0.33 mmoles) of 2,6-lutidine. The solution is stirred for 4 hours under nitrogen at room temperature then 36 mg. (2.0 mmoles) of water is added. The mixture is stirred at room temperature for an additional 1.0 hour then is diluted with ethyl acetate. The diluted solution is washed with 0.1 N hydrochloric acid (1×), with water (1×), and with saturated brine (1×), is dried (anhydrous magnesium sulfate), and is concentrated. Purification of the crude residue by silica gel chromatography affords the 11α,15α-bis-formyl-2-descarboxy-2-(tetrazol-5-yl)PGE$_2$.

EXAMPLE XXXII

2-[2β-(3α-hydroxy-trans-1-octen-1-yl)-3α,5α-dihydroxycyclopent-1α-yl]acetaldehyde, γ-hemiacetal:

To a solution cooled to −78° of 866 mg. (1.93 mmoles) of the known 2-[3α-p-phenylbenzoyloxy-5α-hydroxy-2β-(3α-hydroxy-trans-1-octen-1-yl)cyclopent-1α-yl]acetic acid, γ-lactone in 12 ml. of toluene was added 4.82 ml. (3.88 mmoles) of a 0.805 M solution of diisobutylaluminum hydride in hexane. The reaction was stirred in the cold under nitrogen for 30 minutes then was quenched by the addition of methanol (0.5 ml.). The reaction was let warm to room temperature then was concentrated to a white semisolid. The semisolid was slurried with methanol (3x), was filtered through Celite 545, and was concentrated. Purification of the crude product by silica gel chromatography using mixtures of chloroform:ethyl acetate as eluents afforded the desired 2-[2β-(3α-hydroxy-trans-1-octen-1-yl)-3α,5α-dihydroxycyclopent-1α-yl]acetaldehyde, γ-hemiacetal as a colorless oil weighing 304 mg. (59.5% yield).

The ir spectrum (CHCl$_3$) of the product exhibited strong adsorptions at 970 cm$^{-1}$ (trans olefin) and 3,380 cm$^{-1}$ (OH). The nmr spectrum (CDCl$_3$) showed multiplets at 5.64–5.20 δ (2H) for the trans olefin, at 4.66–4.22 δ (1H) for the O—C$\underline{H}$-O, at 4.18–3.19 δ (3H) for the OC$\underline{H}$, and at 2.62–0.40 δ (2OH) for the remaining protons.

EXAMPLE XXXIII

3α,5α-dihydroxy-2β-(3α-hydroxy-trans-1-octen-1-yl)-1α-[6-(tetrazol-5-yl)-cis-2-hexen-1-yl]cyclopentane:

To a solution 2.91 g. (6.25 mmoles) of [4-(tetrazol-5-yl)-n-butyl]triphenylphosphonium bromide in 3 ml. of dimethyl sulfoxide is added 6.00 ml. (12.0 mmoles) of a 2.0 M solution of sodium methylsulfinylmethide in dimethyl sulfoxide. The resultant red ylide solution is stirred for 10 minutes then a solution of 338 mg. (1.25 mmoles) of the triol of Example XXXII in 2.0 ml. of dimethyl sulfoxide is added dropwise. The mixture is stirred at room temperature under nitrogen for 4 hours then is poured onto a mixture of ethyl acetate ice-water. The aqueous layer is acidified with 10% aqueous hydrochloric acid and is extracted with ethyl acetate; the combined organic extracts are washed with water and saturated brine, are dried (anhydrous magnesium sulfate), and concentrated. Purification of the crude product by silica gel chromatography provides the desired 3α,5α-dihydroxy-2β-(3α-hydroxy-trans-1-octen-1-yl)-1α-[7-(tetrazol-5-yl)-cis-2-hepten-1-yl]cyclopentane. This compound is 2-descarboxy-2-(tetrazol-5-yl)PGF$_2$ α.

EXAMPLE XXXIV

2-[3α-p-phenylbenzoyloxy-2β-(3α-hydroxyoct-1-yl)-5α-hydroxy-cyclopent-1α-yl]acetic acid, γ-lactone A heterogeneous mixtur of 954 mg. (2.14 mmoles) of the known 2-[3α-p-phenylbenzoyloxy-5α-hydroxy-2β-(3α-hydroxy-trans-1-octen-1-yl)cyclopent-1α-yl]acetic acid, γ-hemiacetal and 95 mg. of 10% palladium on carbon in 10 ml. of absolute methanol is stirred under one atmosphere of hydrogen at room temperature for 4.5 hours. The mixture is then filtered through a pad of Celite and concentrated to afford the desired 2-[3α-p-phenylbenzoyloxy-2β-(3α-hydroxyoct-1-yl)-5α-hydroxy-cyclopent-1α-yl]acetic acid, γ-lactone.

This compound may be reduced as described in Example XXXII to 2-[3α,5α-dihydroxy-2β-(3α-hydroxyoct-1-yl)cyclopent-1α-yl] acetaldehyde, γ-hemiacetal.

This compond may be converted to 2-descarboxy-2-(tetrazol-5-yl)-13,14-dihydro PGF$_2$ α following the method of Example XXXIII.

EXAMPLE XXXV

5α-hydroxy-2β-benzyloxymethyl-3α-(tetrahydropyran-2-yloxy)-1α-[6-(tetrazol-5-yl)-cis-1-hexen-1-yl)]cyclopentane To a solution of 7.06 g. (15.0 mmoles) of [4-(tetrazol-5-yl)-butyl]triphenylphosphonium bromide in 14 ml. of dimethyl sulfoxide is added dropwise 15.0 ml. of a 2.0 M solution of sodium methylsulfinylmethide in dimethyl sulfoxide. To the resultant red ylide solution is added dropwise a solution of 1.76 g. (5.0 mmoles) of the known 2-[2β-benzyloxymethyl-3α-(tetrahydropyran-2-yloxy)-5α-hydroxycyclopent-1α-yl]acetaldehyde, γ-hemiacetal in 17 ml. of dimethyl sulfoxide. After being stirred for 12 hours under nitrogen at room temperature the reaction is poured onto ice-water. The aqueous solution is overlaid with ethyl acetate, is acidified to pH~ 3 with 10% aqueous hydrochloric acid, and is extracted with ethyl acetate. The combined ethyl acetate extracts are washed with water, dried (anhydrous magnesium sulfate), and concentrated. Purification of the crude product by silica gel chromatography provides the desired 5α-hydroxy-2β-benzyloxymethyl-3α-(tetrahydropyran-2-yloxy)-1α16-(tetrazol-5-yl)-cis-11-hexen-1-yl]cyclopentane.

EXAMPLE XXXVI

5α-acetoxy-2β-benzyloxymethyl-3α-(tetrahydropyran-2-yloxy)-1α-[6-(tetrazol-5-yl)-cis-1-hexen-1-yl]cyclopentane A mixture of 1.66 g. (3.45 mmoles) of the chromatographed alcohol of Example XXXV, 5.0 ml. of pyridine and 0.736 ml. (7.78 mmoles) of acetic anhydride is stirred under nitrogen at 50° for 18 hours. The mixture is then cooled to room temperature and diluted with ethyl acetate. The organic solution is washed with 10% hydrochloric acid then water, is dried (anhydrous magnesium sulfate), and is concentrated. Purification of the crude product by silica gel chromatography provides the desired 5α-acetoxy-2β-benzyloxymethyl-3α-(tetrahydropyran-2-yloxy)-1α-[6-(tetrazol-5-yl)-cis-1-hexen-1-yl]cyclopentane.

EXAMPLE XXXVII

5α-acetoxy-2β-hydroxymethyl-3α-(tetrahydropyran-2-yloxy)-1α-[6-(tetrazol-5-yl)-hex-1-yl]cyclopentane A heterogeneous mixture of 1.62 g. (3.14 mmoles) of the chromatographed benzyl ether of Example XXXVI, 324 mg. of 5% palladium on carbon, and 16.2 ml. of a 20:1 mixture of absolute ethanol:glacial acetic acid is stirred at room temperature under one atmosphere of hydrogen for 8 hours. The mixture is then filtered through Celite 545 and the filtrate is concentrated and is azeotroped under reduced pressure with toluene. Purification of the crude product by silica gel chromatography affords the desired 5α-acetoxy-2β-hydroxymethyl-3α-(tetrahydropyran-2-yloxy)-1α-[6-(tetrazol-5-yl)-hex-1-yl]cyclopentane.

EXAMPLE XXXVIII

5α-acetoxy-2β-formyl-3α-(tetrahydropyran-241.7 1α-[6-tetrazol-5-yl)-hex-1-yl]cyclopentane then a pad desired To a mechanically stirred solution of 3.37 ml. (41.7 mmoles) of pyridine in 50 ml. of methylene chloride, cooled to 10° to 15° under nitrogen, is added portionwise over a period of 30 minutes 1.89 g. (18.9 mmoles) of chromium trioxide. The dark burgundy solution is let warm to room temperature then is cooled to 0°. To the cold solution is added a solution of 1.01 g. (2.37 mmoles) of the alcohol of Example XXXVII in 7.0 ml. of methylene chloride with the concomitant formation of a dense black precipitate. The suspension is stirred in the cold for 15 minutes then 7.21 g. (52.2 mmoles) of finely ground sodium bisulfite monohydrate is added. After being stirred for 10 minutes 6.52 g. (52.2 mmoles) of anhydrous magnesium sulfate is added. After being stirred for 5 minutes the dark suspension is filtered through a pad of Celite, is washed with methylene chloride, then is concentrated to afford the desired 5α-acetoxy-2β-formyl-3α-(tetrahydropyran-2-yloxy)-1α-[6-(tetrazol-5-yl)-hex-1-yl]cyclopentane which is used without purification.

EXAMPLE XXXIX

5α-acetoxy-2β-(3-oxo-trans-1-octen-1-yl)-3α-(tetrahydropyran-2-yloxy)-1α-[6-(tetrazol-5-yl)-hex-1yl]cyclopentane To a suspension of 220 mg. (5.22 mmoles) of a 57.0% dispersion of sodium hydride in mineral oil in 40 ml. of 1,2-dimethoxyethane is added 1.16 g. (5.22 mmoles) of dimethyl-2-oxoheptylphosphonate. The mixture is stirred at room temperature for 1 hour under nitrogen with the concomitant formation of a dense white precipitate. To this suspension is added a solution of 1.13 g. (2.37 mmoles) of the aldehyde of Example XXXVIII in 4 ml. of 1,2-dimethoxyethane. The solution is stirred at room temperature for 2.0 hours under nitrogen then is quenched by the addition of glacial acetic acid to pH ~5 and is concentrated. Purification of the crude product by silica gel chromatography gives the desired 5α-acetoxy-2β-(3-oxo-trans-1-octen-1-yl)-3α-(tetrahydropyran-2-yloxy)-1α-[6-(tetrazol-5-yl)-hex-1-yl]-cyclopentane.

EXAMPLE XL

5α-acetoxy-2β-(3α-hydroxy-trans-1-octen-1-yl)-3α-(tetrahydropyran-2-yloxy)-1α-[6-(tetrazol-5-yl)-hex-1-yl]cyclopentane 1

To a solution, cooled to −78°, of 852 mg. (2.0 mmoles) of the enone of Example XXXIX in 20 ml. of tetrahydrofuran is added 16 ml. (4.0 mmoles) of a 0.25 M solution of lithium tri-sec butylborohydride in tetrahydrofuran. The solution is stirred at −78° under nitrogen for 1.0 hour then is quenched by the addition of 10 ml. of 40% aqueous acetic acid. The quenched reaction mixture is let warm to room temperature and is extracted with ethyl acetate; the combined organic extracts are washed with water and saturated brine, are dried (anhydrous magnesium sulfate), are concentrated, and azeotroped with toluene. Purification of the crude product by silica gel chromatography provides the 5α-acetoxy-2β-(3α-hydroxy-trans-1-octen-1-yl)-3α-(tetrahydropyran-2-yloxy)-1α-[6-(tetrazol-5-yl)-hex-1-yl]cyclopentane and the 5α-acetoxy-2β-(3β-hydroxy-trans-1-octen-1-yl)-3α-(tetrahydropyran-2-yloxy)-1α-[6-(tetrazol-5-yl)hex-1-yl]cyclopentane.

The 5α-acetoxy-2β-(3β-hydroxy-trans-1-octen-1-yl)-3α-(tetrahydropyran-2-yloxy)-1α-[6-(tetrazol-5-yl)hex-1-yl]cyclopentane may be converted by the procedures in Examples XLI to XLIX to 15-epi-2-descarboxy-2-(tetrazol-5-yl)PGE$_1$ and PGF$_{1\alpha}$.

EXAMPLE XLI

5α-hydroxy-2β-(3α-hydroxy-trans-1-octen-1-yl)-3α-(tetrahydropyran-2-yloxy)-1α-[6-(tetrazol-5-yl)-hex-1-yl]cyclopentane A mixture of 522 mg. (1.00 mmole) of the THP ether of Example XL, 3.0 ml. (3.0 mmoles) of 1.0 N aqueous sodium hydroxide, 3.0 ml. of tetrahydrofuran, and 3.0 ml. of absolute methanol is stirred under nitrogen at room temperature for 1.5 hours. The solution is then acidified by the addition of 3.0 ml. of 1.0 N hydrochloric acid and is extracted with ethyl acetate. The combined extracts are dried (anhydrous magnesium sulfate) and concentrated. Purificantion of the crude product by silica gel chromatography affords the desired 5α-hydroxy-2β-(3α-hydroxy-trans-1-octen-1-yl)-3α-(tetrahydropyran-2-yloxy)-1α-[6-(tetrazol-5-yl)-hex-1-yl]cyclopentane.

EXAMPLE XLII

5α-hydroxy-2β-(3α-hydroxy-trans-1-octen-1-yl)-3α-hydroxy-1α-[6-(tetrazol-5-yl)-hex-1-yl]cyclopentane A solution of 500 mg. of the THP ether of Example XLI in 5 ml. of a 65:35 mixture of glacial acetic acid:water is stirred at room temperature under nitrogen for 18 hours then is concentrated and azeotroped under reduced pressure with toluene. Purification and the crude product by silica gel chromatography gives the desired 5α-hydroxy-2β-(3α-hydroxy-trans-1-octen-1-yl)-3α-hydroxy-1α-[6-(tetrazol-5-yl)-hex-1-yl]cyclopentane.

EXAMPLE XLIII

5α-acetoxy-2β-(3α-hydroxy-trans-1-octen-1-yl)-3α-hydroxy-1α-[6-(tetrazol-5-yl)-hex-1-yl]cyclopentane.

A solution of 1.13 g. (2.16 mmoles) of the THP ether of Exaple XXXIX in 11 ml. of a 65:35 mixture of acetic acid:water is stirred at room temperature under nitrogen for 18 hours then is concentrated and azeotroped under reduced pressure with toluene. Purification of the crude product by silica gel chromatograhy provides the desired 5α-acetoxy-2β-(3α-hydroxy-trans-1-octen-1-yl)-3α-hydroxy-1α-[6-(tetrazol-5-yl)-hex-1-yl]cyclopentane.

EXAMPLE XLIV

5α-hydroxy-2β-(3α-hydroxy-trans-1-octen-1-yl)-3α-hydroxy-1α-[6-(tetrazol-5-yl)-hex -1-yl]cyclopentane:

A solution of 424 mg. (1.00 mmole) of the diol of Example XLIII, 3.0 ml. (3.0 mmoles) of 1.0 N aqueous sodium hydroxide, 3.0 ml. of tetrahydrofuran, and 3.0 ml. of absolute methanol is stirred under nitrogen at room temperature for 2.5 hours. The solution is then acidified by the addition of 3.0 ml. of 1.0 N hydrochloric acid and is extracted with ethyl acetate. The combined organic extracts are dried (anhydrous magnesium sulfate) and concentrated. Purification of the crude product by silica gel chromatography provides the desired 5α-hydroxy-2β-(3α-hydroxy-trans-1-octen-1-yl)-3α-hydroxy-1α-[6-(tetrazol-5-yl)-hex-1-yl]cyclopentane.

EXAMPLE XLV

5α-acetoxy-2β-(3α-(tetrahydropyran-2-yloxy)-trans-1-octen-1-yl)-3α-(tetrahydropyran-2-yloxy)-1α-[6-(tetrazol-5-yl)-hex-1-yl]-cyclopentane.

A solution of 250 mg. of the alcohol of Example XL, 0.250 ml. of dihydropyran, 2.5 ml. of methylene chloride, and 2.5 mg. of p-toluenesulfonic acid monohydrate is stirred at room temperature under nitrogen for 15 minutes. The reaction mixture is then diluted with ether, is washed with water, is dried (anhydrous magnesium sulfate), and is concentrated to provide the desired 5α-acetoxy-2β-(3α-(tetrahydropyran-2-yloxy)-trans-1-octen-1-yl)-3α-(tetrahydropyran-2-yloxy)-1α-[6-(tetrazol-5-yl)-hex-1-yl]cyclopentane.

EXAMPLE XLVI

5α-hydroxy-2β-(3α-(tetrahydropyran-2-yloxy)-trans-1-octen-1-yl)-3α-(tetrahydropyran-2-yloxy)-1α-[6-(tetrazol-5-yl)-hex-1-yl]-cyclopentane.

A homogeneous solution of 0.265 g. (0.436 mmole) of the crude bis-THP ether of Example XLV, 1.30 ml. (1.30 mmoles) of a 1.0 N aqueous sodium hydroxide solution, 1.3 ml. of methanol, and 1.3 ml. of tetrahydrofuran is stirred at room temperature overnight. The reaction mixture is then quenched by the addition of 1.30 ml. (1.30 mmoles) of a 1.0 N aqueous hydrochloric acid solution and is diluted with ethyl acetate. The organic layer is dried (anhydrous magnesium sulfate) and concentrated. Purification of the crude product by silica gel chromatograhy affords the desired 5α-hydroxy-2β-(3α-(tetrahydropyran-2-yloxy)-trans-1-octen-1-yl)-3α-(tetrahydropyran-2-yloxy)-1α-[6-(tetrazol-5-yl)-hex-1-yl]cyclopentane.

EXAMPLE XLVII

5α-hydroxy-2β-(3α-hydroxy-trans-1-octen-1-yl)-3α-hydroxy-1α-[6-(tetrazol-5-yl)-hex-1-yl]cyclopentane.

A solution of 75 mg. of the alcohol of Example XLVI in 1.0 ml. of a 65:35 mixture of glacial acetic acid:water is stirred under nitrogen at room temperature for 20 hours, then is concentrated and azeotroped with toluene. Purification of the crude product by silica gel chromatography gives the desired 5α-hydroxy-2β-(3α-hydroxy-trans-1-octen-1-yl)-3α-hydroxy-1α-[6-(tetrazol-5-yl)-hex-1-yl]cyclopentane.

EXAMPLE XLVIII

4α-(tetrahydropyran-2-yloxy)-2α-[6-(tetrazol-5-yl)-hex-1-yl]-3β-(3α-(tetrahydropyran-2-yloxy)-trans-1-octen-1-yl)cyclopentanone To a solution, cooled to −23° under nitrogen, of 0.202 g. (0.371 mmole) of the alcohol of Example XLVI in 4.0 ml. of acetone is added dropwise 0.163 ml. (0.408 mmole) of Jones' reagent. The reaction is stirred in the cold for 15 minutes then is quenched by the addition of 0.163 ml. of isopropyl alcohol. The quenched reaction is stirred in the cold for 5 minutes then is diluted with ethyl acetate. The organic solution is washed with water, is dried (anhydrous magnesium sulfate), and is concentrated to afford the desired 4α-(tetrahydropyran-2-yloxy)-2α-[6-(tetrazol-5-yl)-hex-1-yl]-3β-(tetrahydropyran-2-yloxy)-trans-1-octen-1-yl)cyclopentanone which is used without purification.

EXAMPLE XLIX

4α-hydroxy-2α-[6-(tetrazol-5-yl)-hex-1-yl]-3β-(3α-hydroxy-trans-1-octen-1-yl)cyclopentanone A homogeneous solution of 0.190 g. of the crude bis-THP ether of Example XLVIII in 2.0 ml. of a 65:35 mixture of glacial acetic acid:water is stirred under nitrogen at room temperature for 12 hours, then is concentrated and azeotroped with toluene. Purification of the crude product by silica gel chromatography affords the desired 4α-hydroxy-2α-[6-(tetrazol-5-yl)-hex-1-yl]-3β-(3α-hydroxy-trans-1-octen-1-yl)cyclopentanone.

EXAMPLE L

To a suspension 275 mg. (6.53 mmoles) of a 57.0% dispersion of sodium hydride in mineral oil in 50 ml of dry 1,2-dimethoxyethane is added 1.63 g. (6.53 mmoles) of the phosphonate of Example XXIX. The solution is stirred at room temperature for 1 hour under nitrogen, then a solution of 1.42 g. (2.96 mmoles) of the aldehyde of Example XXXVIII in 6 ml. of 1,2-dimethoxyethane is added. The solution is stirred at room temperature for 2.0 hours under nitrogen then is quenched by the addition of glacial acetic acid to pH ∼ 5 and is concentrated. Purification of the crude product by silica gel chromatography provides the desired 5α-acetoxy-2β-(3-oxo-4,4-dimethyl-trans-1-octen-1-yl)-3α-(tetrahydropyran-2-yloxy)-1α-[6-(tetrazol-5-yl)hex-1-yl]cyclopentane.

This product is converted by the procedures of Examples XL to XLIX to 2-descarboxy-2-(tetrazol-5-yl)-16,16-dimethyl $PGE_1$ and $PGF_1$ and 15-epi-2-descarboxy-2-(tetrazol-5-yl)-16,16-dimethyl $PGE_{1\alpha}$ and $PGF_{1\alpha}$.

What is claimed is:

1. A compound of the structure:

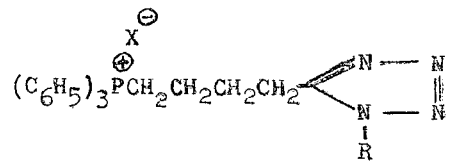

wherein R is hydrogen or alkyl having from 1 to 3 carbon atoms; and

X is chlorine, bromine, or iodine.

2. A compound of the structure:

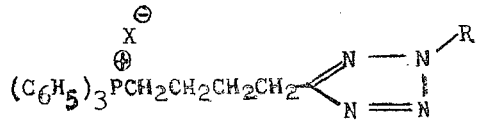

wherein R is hydrogen or alkyl having from 1 to 3 carbon atoms; and
X is chlorine, bromine, or iodine.

3. A compound according to claim 1 wherein R is hydrogen and X is bromine.

4. A compound according to claim 1 wherein R is methyl and X is bromine.

5. A compound according to claim 2 wherein R is methyl and X is bromine.

* * * * *